US011219682B2

(12) United States Patent
Ni

(10) Patent No.: US 11,219,682 B2
(45) Date of Patent: Jan. 11, 2022

(54) DPS FUSION PROTEINS FOR USE IN VACCINES AND DIAGNOSTICS

(71) Applicant: KJ Biosciences LLC, College Station, TX (US)

(72) Inventor: Yawei Ni, College Station, TX (US)

(73) Assignee: KJ Biosciences LLC, College Station, TX (US)

( * ) Notice: Subject to any disclaimer, the term of this patent is extended or adjusted under 35 U.S.C. 154(b) by 0 days.

(21) Appl. No.: 15/893,261

(22) Filed: Feb. 9, 2018

(65) Prior Publication Data

US 2018/0333478 A1 Nov. 22, 2018

Related U.S. Application Data

(63) Continuation of application No. 14/967,729, filed on Dec. 14, 2015, now Pat. No. 9,889,190, which is a continuation of application No. 13/520,253, filed as application No. PCT/US2010/061906 on Dec. 22, 2010, now Pat. No. 9,241,986.

(60) Provisional application No. 61/335,737, filed on Jan. 11, 2010, provisional application No. 61/335,283, filed on Jan. 4, 2010.

(51) Int. Cl.

| | |
|---|---|
| ***A61K 39/145*** | (2006.01) |
| ***A61K 39/39*** | (2006.01) |
| ***C07K 14/005*** | (2006.01) |
| ***C07K 14/11*** | (2006.01) |
| ***C07K 14/195*** | (2006.01) |
| ***A61K 39/12*** | (2006.01) |
| ***C07K 14/245*** | (2006.01) |
| ***A61K 39/00*** | (2006.01) |
| ***A61K 39/21*** | (2006.01) |
| ***C07K 14/47*** | (2006.01) |
| ***C12N 7/00*** | (2006.01) |

(52) U.S. Cl.

CPC ........ *A61K 39/145* (2013.01); *A61K 39/0011* (2013.01); *A61K 39/12* (2013.01); *A61K 39/21* (2013.01); *A61K 39/39* (2013.01); *C07K 14/005* (2013.01); *C07K 14/11* (2013.01); *C07K 14/195* (2013.01); *C07K 14/245* (2013.01); *C07K 14/4748* (2013.01); *C12N 7/00* (2013.01); *A61K 2039/55555* (2013.01); *A61K 2039/55566* (2013.01); *A61K 2039/6068* (2013.01); *C07K 2319/00* (2013.01); *C07K 2319/33* (2013.01); *C12N 2710/20022* (2013.01); *C12N 2710/20034* (2013.01); *C12N 2740/16122* (2013.01); *C12N 2760/16022* (2013.01); *C12N 2760/16034* (2013.01); *C12N 2760/16071* (2013.01); *C12N 2760/16122* (2013.01)

(58) Field of Classification Search

None

See application file for complete search history.

(56) References Cited

U.S. PATENT DOCUMENTS

| | | | |
|---|---|---|---|
| 7,608,268 | B2 | 10/2009 | Carter et al. |
| 9,241,986 | B2 | 1/2016 | Ni |
| 2007/0224205 | A1 | 9/2007 | Powell et al. |
| 2007/0258889 | A1 | 11/2007 | Douglas et al. |

FOREIGN PATENT DOCUMENTS

| | | |
|---|---|---|
| WO | 2009/0120380 | 10/2009 |

OTHER PUBLICATIONS

Hanna et al., Evidence for glycosylation on a DNA-binding protein of *Salmonella enterica*, 2007, Micrbial Cell Factories, vol. 6, No. 11, pp. 1-10.*

Almiron et al., A novel DNA-binding protein with regulatory and protective roles in starved *Escherichia coli*, Genes Dev., 6:2646-2654 (1992).

Beignon et al., A peptide vaccine administered transcutaneously together with cholera toxin elicits potent neutralising anti-FMDV antibody responses, Vet. Immunol Immunopathol., 104:273-280 (2005).

Brandt et al., Key epitopes on the ESAT-6 antigen recognized in mice during the recall of protective immunity to Mycobacterium tuberculosis, J. Immunol., 157:3527-3533 (1996).

Bullough et al., Structure of influenza haemagglutinin at the pH of membrane fusion, Nature, 371:37-43 (1994).

Burton et al., A Boost for HIV Vaccine Design, Science, 329:770-773 (2010).

Caldeira et al., Immunogenic display of diverse peptides, including a broadly crosstype neutralizing human papillomavirus L2 epitope, on virus-like particles of the RNA bacteriophage PP7, Vaccine, 28:4384-4393 (2010).

Chackerian, Virus-like particles: flexible platforms for vaccine development, Expert Rev. Vaccines, 6:381-390 (2007).

Cheever et al., The Prioritization of Cancer Antigens: A National Cancer Institute Pilot Project for the Acceleration of Translational Research, Clin. Cancer Res. ,15:5323-5337 (2009).

Chun et al., Universal antibodies and their applications to the quantitative determination of virtually all subtypes of the influenza A viral hemagglutinins, Vaccine, 26:6068-6076 (2008).

De Bernard et al., The immune modulating activity of the Helicobacter pylori HP-NAP: Friedn or Foe? Toxicon, 56:1186-1192 (2010).

Denis et al., Development of a universal influenza A vaccine based on the M2e peptide fused to the papaya mosaic virus (PapMV) vaccine platform, Vaccine, 26:3395-3403 (2008).

Ekiert et al., Antibody Recognition of a Highly Conserved Influenza Virus Epitope, Science, 324:246-251 (2009).

Hiers et al., M2e-based universal influenza A vaccine, Vaccine, 27:6280-6283 (2010).

FDA influenza vaccine list, accessed on line at http://www.fda.gov/BiologicsBloodVaccines/SafetyAvailabillity/VaccineSafety/ucm110288.htm accessed on Nov. 30, 2013.

(Continued)

*Primary Examiner* — Benjamin P Blumel

(74) *Attorney, Agent, or Firm* — Meunier Carlin & Curfman LLC

(57) ABSTRACT

Novel nanoparticle fusion proteins comprising proteins or peptides fused to Dps (DNA binding protein from starved cells) proteins are provided which bring forth distinct advantages for development of new and improved vaccines, diagnostic tests, and other biomedical products.

9 Claims, 8 Drawing Sheets

Specification includes a Sequence Listing.

(56) References Cited

OTHER PUBLICATIONS

Foo et al., Identification of neutralizing linear epitopes from the VP1 capsid protein of Enterovirus 71 using synthetic peptides, Virus Res., 125:61-68 (2007).
Galili et al., A unique natural human IgG antibody with anti-α-Galactosyl specificity, J. Exp. Med., 160:1519-1531 (1984).
Gauss et al., Structure of the DPS-Like Protein from Sulfolobus solfataricus Reveals a Bacterioferritin-Like Dimetal Binding Site within a DPSLike Dodecameric Assembly, Biochemistry, 45:10815-10827 (2006).
Genebank ID AE006642.1.
Genebank ID AF536179.1.
Genebank ID CY033622.1.
Genebank ID CY033623.1.
Genebank ID X69337.1.
Grant et al., The crystal structure of Dps, a ferritin homolog that binds and protects DNA, Nat. Struct. Biol., 5(4):294-303 (1998).
Grgacic et al., Virus-like particles: passport to immune recognition, Methods, 40:60-65 (2006).
Haikarainen et al., Dps-like proteins: structural and functional insights into a versatile protein family, Cell Mol. Life Sci., 67:341-351 (2010).
Heddle, Protein cages, rings and tubes: useful components of future nanodevices? Nanotechnology, Science and Applications, 1:67-78 (2008).
Heiny et al., Evolutionarily Conserved Protein Sequences of Influenza A Viruses, Avian and Human, as Vaccine Targets, PLoS One, 2: e1190 (2007).
Henion, et al., "Synthesis of a-gal epitopes on influenza virus vaccines, by recombinant a1,3galactosyltransferase, enables the formation of immune complexes with the natural anti-Gal antibody", Vaccine 15:11, 1174-1182 (1997).
Huleatt et al., Potent immunogenicity and efficacy of a universal influenza vaccine candidate comprising a recombinant fusion protein linking influenza M2e to the TLR5 ligand flagellin, Vaccine, 26:201-214 (2007).
Ilari et al., The dodecameric ferritin from Listeria innocua contains a novel intersubunit iron-binding site, Nat. Struct. Biol., 7:3 8-43 (2000).
International Search Report for Application No. PCT/US2010/061906 dated Mar. 11, 2011.
Ionescu et al., Pharmaceutical and immunological evaluation of human papillomavirus viruslike particle as an antigen carrier, J. Phamr. Sci., 95:70-79 (2006).
Jakubovics et al., Differential binding specificities of oral streptococcal antigen I/II family adhesins for human or bacterial ligands, Mol. Biol., 55(5):1591-1605 (2005).
Kanodia et al., Peptide-based vaccines for cancer: realizing their potential, Expert Rev. Vaccines, 7:1533-1545 (2008).
Karanam et al., Developing vaccines against minor capsid antigen L2 to prevent papillomavirus infection, Immunol. Cell Biol., 87:287-299 (2009).
Kim et al., Crystal Structure of Dps-1, a Functionally Distinct Dps Protein from Deinococcus radiodurans, J. Mol. Biol., 361:105-114 (2006).
Kim et al., Crystal structure of a small heat-shock protein, Nature, 394:595-599 (1998).
Neirynck et al., A universal influenza A vaccine based on the extracellular domain of the M2 protein, Nat. Med., 5:1157-1163 (1999).
Oka et al., WT1 peptide vaccine for the treatment of cancer, Curr. Opinion in Immunol., 20:211-220 (2008).
Oscherwitz at al., A Synthetic Peptide Vaccine Directed against the 2β2-2β2 Loop of Domain 2 of Protective Antigen Protects Rabbits from Inhalation Anthrax, J. Immunol., 185:3661-3668 (2010).
Paek et al., Development of rapid one-step immunochromatographic assay, Methods, 1:53-60 (2000).
Piao et al., Induction of paranodal myelin detachment and sodium channel loss in vivo by Campylobacter jejuni DNA-binding protein from starved cells (C-Dps) in myelinated nerve fibers, J. Neurol. Sci., 288:54-62 (2010).
Pozsgay et al., Conjugation Methods Toward Synthetic Vaccines, Carbohyrdate-Based Vaccin, René Roy (ed.)., pp. 36-70, ACS Symposium Series 989, Washington DC. (2008).
Pumpens et al., Hepatitis B core particles as a universal display model: a structure-function basis for development, FEBS Letters, 442:1-6 (1999).
Roy et al., Role of N and C-terminal Tails in DNA Binding and Assembly in Dps: Structural Studies of Mycobacterium smegmatis Dps Deletion Mutants, J. Mol. Biol., 370:752-767 (2007).
Santosuosso et al., Intranasal Boosting with an Adenovirus-Vectored Vaccine Markedly Enhances Protection by Parenteral Mycobacterium bovis BCG Immunization against Pulmonary Tuberculosis, Infect. Irnmun., 74:4634-4643 (2006).
Shi et al., Structural Characterization of HIV gp41 with the Membrane-proximal External Region, J. Biol. Chem., 285:24290-24298 (2010).
Stillman et al., The crystal structures of Lactococcus lactis MG1363 Dps proteins reveal the presence of an N-terminal helix that is required for DNA binding, Mol. Microbiol., 57(4): 1101-1112 (2005).
Swalley et al., Full-Length Influenza Hemagglutinin HA2 Refolds into the Trimeric Low-pH-Induced Conformation, Biochemistry, 43:5902-5911 (2004).
Teneberg et al., Carbohydrate Binding Specificity of the Neutrophil-activating Protein of Helicobacter pylori, J. Biol. Chem., 272:19067-19071 (1997).
Verdoliva et al., Simplified β-amyloid peptides for safer Alzheimer vaccines development, Human Vaccines, 6(11):936-947 (2010).
W1edenheft et al., An archaeal antioxidant: Characterization of a Dps-like protein from Sulfolobus solfataricus,. Proc. Nat'l Acad. Sci. USA, 102:10551-10556 (2005).
Weidenheft et al., Bioprospecting in high temperature environments; application of thermostable protein cages, Soft Matter, 3:1091-1098 (2007).
Zhao et al., Iron and Hydrogen Peroxide Detoxification Properties of DNA-binding Protein from Starved Cells. A Ferritin-Like DNA-Binding Protein of *Escherichia coli*, J. Biol. Chem., 277:27689-27696 (2002).
Schellenbacher et al., Chimeric L1-L2 Virus-Like Particles as Potential Broad-Spectrum Human Papillomavirus Vaccines. J of Virology 2009, 10085-10095.

* cited by examiner

DPS FUSION PROTEINS FOR USE IN VACCINES AND DIAGNOSTICS

CROSS-REFERENCE TO RELATED APPLICATIONS

This application is a Divisional of U.S. patent application Ser. No. 14/967,729, filed Dec. 14, 2015, which is a Continuation of U.S. patent application Ser. No. 13/520,253, filed Jul. 2, 2012, which is a national stage entry of International Application Number PCT/US2010/061906 filed Dec. 22, 2010, which claims the benefit of Provisional Application No. 61/335,737 filed Jan. 11, 2010, and Provisional Application No. 61/335,283 filed Jan. 4, 2010, the disclosures of which are incorporated herein by reference in their entirety.

FIELD OF THE INVENTION

The present invention relates generally to the field of medicine, and specifically to microbiology, immunology, diagnostics, and vaccines, and more specifically, diagnosis, treatment, and prevention of diseases by using Dps fusion proteins.

BACKGROUND OF THE INVENTION

DDs Proteins

DNA-binding proteins from starved cells (Dps) are a family of well conserved proteins found in bacteria and archaea, but not in animals or humans. They are responsible for protecting cellular DNA against free radicals under stress conditions. Dps is a dodecameric nanoparticle consisting of 12 identical subunits arranged in a 2:3 symmetry. It has a diameter of 9 nm with an inner cavity of 4.5 nm in diameter (Grant et al., Nat Struct. Biol. 5:294-303, 1998). The Dps of *Escherichia coli* (*E. Coli*) is the prototype of Dps, which was first discovered in 1992 by Almiron et al (Genes Dev 6:2646-2654, 1992). The expression of Dps is increased when cells are under stress or starved conditions (Almiron et al., Genes Dev 6:2646-2654, 1992).

Each Dps subunit has a molecular weight of ~20 kDa and folds into a compact four-helix bundle with free N- and C-termini located at the opposite end (Grant et al., Nat Struct Biol 5:294-303, 1998; Roy et al., J Mol Biol. 370:752-67, 2007; Haikarainen and Papageorgiou. Cell Mol Life Sci. 67:341-51, 2010). The four helixes are inter-connected together by three loop sequences of variable lengths. A short helix may also be formed in the free N-terminus. Twelve copies of the Dps subunit are assembled into a 9 nm nanoparticle according to a 2:3 symmetry with both free N- and C-terminal sequences exposed on the surface (Grant et al., Nat Struct Biol 5:294-303, 1998; Stillman et al., Mol Microbiol. 57:1101-12, 2005; Roy et al., J Mol Biol. 370: 752-67, 2007; Haikarainen and Papageorgiou. Cell Mol Life Sci. 67:341-51, 2010). Crystal structures of Dps from several bacteria and archaea have been determined, including *E. Coli* (Grant et al., Nat Struct Biol 5:294-303, 1998), *Sulfolobus solfataricus* (Gauss et al., Biochemistry, 45:10815-10827, 2006), *Mycobacterium smegmatis* (Roy et al., J Mol Biol. 370:752-67, 2007). *Deinococcus radiodurans* (Kim et al., J. Mol. Biol. 361:105-114, 2006). *Lactococcus lactis* (Stillman et al., Mol Microbiol. 57:1101-12, 2005) and *Listeria innocua* (Ilari et al., Nat Struct Biol. 7:38-43, 2000). It is understood from these structural analyses that the free N- and C-terminal sequences of Dps, especially the amino acids at the very end of these terminal sequences, are often either not or only partially observed in the electron density maps. Thus, while the overall terminal sequences may be present on the surface, the very end of terminal sequences may possibly extend into the interior of the Dps structure. This is illustrated in the case of *Sulfolobus solfataricus* Dps (SsDps) where a few C-terminal amino acids observed in the density map that are before those unobserved ones at the very end were found pointing toward the interior of the nanoparticle structure (Gauss et al., Biochemistry, 45:10815-10827, 2006).

Dps protects DNA against the oxidative stress through iron binding and DNA binding (Zhao et al., J Biol Chem 277:27689-27696, 2002; Haikarainen and Papageorgiou. Cell Mol Life Sci. 67:341-51, 2010). Binding $Fe^{2+}$ ions prevents generation of toxic hydroxyl radicals through Fenton reaction that damage DNA. The iron binding is mediated by a unique di-iron metal binding site located at the interface between subunits comprising the conservative amino acids histidine (His), aspartic acid (Asp), and glutamic acid (Glu). DNA binding provides the physical protection of DNA. The N- or C-termini of Dps in many members of Dps is rich in basic amino acids and involved in the DNA binding through ionic interaction (Ceci et al., Acids Res. 32:5935-5944, 2004; Roy et al. J Mol Biol. 470:752-67, 2007).

While the dodecameric nanoparticle structure is well conserved among all Dps, the Dps primary amino acid sequences vary widely among different families of bacteria or archaea. For example, Dps of *E. Coli* (Swiss-Prot Accession #P0ABT2) only shares <30% amino acid sequence identity with Dps from hyperthermophilic archaeon *Sulfolobus Solfataricus* (Swiss-Prot Accession #P95855), extremophilic bacterium *Deinococcus radiodurans* (Swiss-Prot Accession #Q9RS64), *Listeria innocua* (Swiss-Prot Accession #P80725), *Helicobacter pylori* (Swiss-Prot Accession #P43313) or *Streptococcus pneumonia* (Swiss-Prot Accession #B1S132). Considering that Dps has been found in nearly all bacteria examined, it is remarkable that there are such genetically diverse sources of Dps. On the other hand, Dps amino acid sequences are very conserved within a bacterial family. For example, the amino acid homology of the Dps among members of enterobacteriaceae, such as *Shigella dysenteriae* (Swiss-Prot Accession #Q32191), *Salmonella typhimurium* (Swiss-Prot Accession #Q7CQV9), *E. Coli* (Swiss-Prot Accession #P0ABT2), and *Klebsiella pneumoniae* (Swiss-Prot Accession #Q84FI02) are above 90%.

The Dps of pathogenic bacteria may also be involved in their pathogenicity. Thus, the Dps of *Helicobacter pylori*, also known as neutrophil-activating protein (HP-NAP), is chemotactic for neutrophils and is involved in the inflammatory reactions (Teneberg et al., J Biol Chem. 272: 19067-19071, 1997). The Dps of *Campylobacter jejuni*, which shares significant homology with HP-NAP, has been shown to bind to sulfatide and may be involved in causing the axonal damage (Piao et al., J Neurol Sci. 288:54-62, 2010).

Vaccines

Vaccines are biologic products for prevention and treatment of infectious diseases, cancers, and other disease conditions. In most cases, vaccines have been developed against infectious diseases which may be caused by bacteria, viruses, or other microorganisms. The antigen is the active component of the vaccine and made of either the whole or a part of a microorganism. Proteins on the surface of microorganisms are often the most important antigens that can generate the protective immune responses against the microorganisms. The internal proteins from microorganisms are also capable of inducing a protective effect, especially through induction of the cellular immunity. The protein antigens can be isolated directly from the microorganisms or produced in an expression host as a recombinant protein. The critical parts of a protein antigen for induction of protective immunity are often represented by short stretches of amino acids or peptides in the protein sequence. They may be identified by its function such as cell binding, cell fusion, and neutralization through systemically testing individual peptides along the entire protein sequence and comparative sequence analysis. Such antigenic peptides, usually less than 100 amino acids long, are better defined as compared to the complex protein antigens and can also be synthesized chemically. Often these peptide antigens are highly conserved among different serotypes and strains of a microorganism and thus able to produce the cross-protective effect. Thus, great efforts are being made in identifying and using these peptide antigens to produce vaccines that may provide a universal protection. These efforts are particularly relevant to microorganisms that are known to undergo frequent genetic changes and/or consist of multiple serotypes, including influenza virus, human immunodeficiency virus (HIV), and human papillomavirus (HPV). Examples of highly conserved peptides include, but not limited to, M2e of influenza virus (Neirynck et al., Nat. Med., 5, 1157-1163, 1999), L2 protein peptides (aa17-36 and aa108-120) of HPV (Karanam et al., Immunol. Cell Bio. 87:287-299, 2009), gp41 peptides of human immunodeficiency virus (HIV) (Shi et al., J Biol Chem. 285:24290-24298, 2010), and fusion peptides of various lengths (14-30 aa) from surface glycoproteins of enveloped viruses (e.g., influenza, HIV, and respiratory syncytial virus). Many other highly conserved peptide sequences have also been identified in other influenza viral proteins as potential vaccine targets (Heiny et al., PLoS One. 2:e1190, 2007; Ekiert et al. Science. 324:246-251, 2009).

There are also pathogens with limited number of serotypes, but possess immunodominant epitopes such as ESAT-6 protein (95 aa) and Ag85A of *Mycobacterium tuberculosis* (TB) (Brandt et al., J. Immunol. 157:3527-3533, 1996; Santosuosso, M et al. Infect. Immun 74: 4634, 2006). Other examples of peptide antigens include those from foot and mouth disease virus (Beignon et al., Vet Immunol Immunopathol. 104:273-80, 2005), malaria (Mahajan et al., Infect Immun. September, 2010), enterovirus 71 (Foo et al., Virus Res. 125: 61-68, 2007), protective antigen of anthrax (Oscherwitz at al., J. Immunol. 185:3661-3668, 2010) and bacterial adhesion peptides (Yakubovics, N. et al. Mol. Biol. 55.1591, 2005).

Besides infectious diseases, peptide-based vaccines are also being developed for cancers and other disease conditions. Small peptides derived from the tumor associated antigen (TAA) have been identified as vaccine candidates against tumors or cancers (Kanodia and Kast, Expert Rev Vaccines. 7:1533-1545, 2008; Cheever et al. Clin Cancer Res. 15:5323-37, 2009; Oka et al., Curr. Opinion in Immunol. 20:211-220). They include the peptides from the WT1 protein of various cancers, the GP2 peptide from breast cancer-related HER2/neu protein, NY-ESO1 from prostate cancer, and various peptides from melanoma. In addition, β-amyloid peptides are used as candidate vaccines for Alzheimer's disease (Lemere, Prog Brain Res. 175:83-93, 2009; Verdoliva et al., Human Vaccines. 6:1-2, 2010).

However, peptide antigens are often poor immunogens on their own for induction of immune responses. To overcome this disadvantage, the peptide antigens may be linked to a carrier protein chemically or as a fusion protein using the recombinant DNA techniques to enhance the immune response against them.

Diagnostics

A diagnostic agent is an agent used in a diagnostic test for diagnosis of an infectious or non-infectious disease. It can be an antigen for detection of specific antibodies or a ligand for binding to or detection of receptor or vice versa. The diagnostic agent also includes specific antibodies for detection of specific antigen or tissues or pathogens associated with the specific antigen. The specific antibodies, either monoclonal or polyclonal, may be raised with the antigen in an animal. A monoclonal antibody is obtained by fusion of spleen cells from an immunized animal with myeloma cells such as SP2/0.

The conserved protein or peptide antigens from a pathogen or disease condition can be very useful as a diagnostic agent. Their use in diagnostic tests can be greatly improved if they are linked or fused to a carrier protein. This is especially true for the peptide antigens as the carrier protein can facilitate attachment of the peptide antigens to the test surface or generation of specific antibodies against them. It is particularly advantageous if two different peptide antigens from the same pathogen or disease are linked with the same carrier protein as this can greatly increase detection sensitivity as well as specificity.

The diagnostic test can be an immunoassay for detection of antigen or antibody, or a test for detection of ligand-receptor binding. ELISA (enzyme-linked immunosorbent assay) is an example of immunoassays. The immunoassays can also be in the dipstick format (Paek et al., Methods. 1:53-60, 2000). The diagnostic agent is often linked with a signal agent or emitter that gives out a measurable signal if the test result is positive. The signal agent can be an enzyme such as alkaline phosphatase, gold particles, and small molecules such as biotin and a fluorescent dye. The signal agent may be linked to the diagnostic agent by chemical conjugation or fusion by recombinant DNA techniques.

Carrier Proteins for Fusion Proteins

Covalent linkage with a carrier protein is an effective approach in enhancing the immunogenicity of vaccine antigens, especially those made with peptides which are poorly immunogenic on their own. Thus, chemical conjugation of small proteins or peptides to the keyhole limpet hemocyanin (KLH) has been a common approach in generating immune responses against them. Linking a peptide to a carrier protein may also be achieved by fusion using recombinant DNA techniques or direct DNA synthesis for linking the DNA sequences coding for the antigens with that for the carrier protein. Various proteins have been used as the carrier proteins for fusion or chemical conjugation with protein or peptide antigens, including KLH, complement, cholerea toxin, tetanus toxoid, OMPC (outer membrane protein complex from *Neisseria meningitides*), thioredoxin, flagellin (Huleatt et al., Vaccine 26:201-14, 2007), virus-like particles (VLPs) of various enveloped and non-enveloped viruses, and nanoparticle proteins such as heat shock protein (Kim et al. Nature. 394:595-9, 1998) and ferritin (U.S. Pat. No. 7,608,268). Some of these carrier proteins also act as an adjuvant such as complement and flagellin which is a ligand for Toll-like receptor 5.

VLPs have been widely tested as a carrier protein. They can be derived from many different enveloped and non-enveloped viruses (Chackerian, Expert Rev Vaccines. 6:381-90, 2007), including papillomavirus (HPV; Ionescu et al., J. Phamr. Sci. 95, 70-79, 2006), hepatitis B core antigen (Hbc; Pumpens and Grens, 1998. FEBS letters 442, 1-6), *papaya* mosaic virus (Denis et al., Vaccine, 26:3395-3403, 2008), and bacteriophage (Caldeira et al., Vaccine, 28:4384-4393). They are primarily made of the virus capsid protein that makes up virus capsid structure. Most of these VLPs are produced by using eukaryotic expression systems such as baculovirus and yeast (Grgacic and Anderson, Methods. 40:60-65, 2006). Most of these VLPs are also nanoparticles (≤100 nm). Thus, the term nanoparticle carrier protein used herein refers to both VLPs and other non-viral nanoparticle carrier proteins.

Nanoparticle carrier proteins are made of multiple subunits, and these subunits self assemble into nanoparticles once expressed in an expression host. Being nanoparticles with multiple subunits, they are highly efficient for antigen presentation and induction of immune responses. This is because the presence of multiple copies of protein or peptide antigens on each particle enhances the antigen presentation. In addition, an antigen in a particulate form is more immunogenic than the free antigen as it can be more efficiently phagocytosed or taken up by the antigen presenting cells.

The Hbc has been widely used as a carrier protein for fusion protein vaccines. For example, the M2e peptide (24 aa) from influenza M2 protein has been fused to the Hbc (Fiers et al., Vaccine 27:6280-6283, 2010), and the resulting fusion protein is capable of inducing immune responses against the peptide. In most cases, protein or peptide antigens are linked to its surface loops of HBc which are well exposed on the surface and can accommodate the inserted proteins or peptides without disrupting the particle formation (Pumpens and Grens, 1998. FEBS letters 442, 1-6). Ferritin is an iron binding nanoparticle protein like Dps, but consists of 24 subunits of different isoforms (H and L chains). U.S. Pat. No. 7,608,268 described fusion of proteins or peptides with ferritin at the N- and/or C-terminus, and the resulting fusion protein retaining the ability to assemble into a polymeric aggregate or capsid assembly. While the N-terminus of ferritin is exposed on the surface, its C-terminus is located in the inner core. Thus, the fused protein or peptide at the N-terminus is exposed on the surface (exocapsid fusion), whereas the one at the C-terminus is embedded within the ferritin particle (endocapsid fusion). Thus, fusion at the C-terminus of ferritin is therefore not suited for surface presentation of the fused antigens to induce direct and immediate immune responses.

Using well established recombinant DNA techniques and direct DNA or gene synthesis, any proteins or peptides can be fused to any sites of another protein. However, what is not known is whether the resulting fusion protein can achieve the desired effect of fusion. Thus, an important requirement for generating fusion proteins with nanoparticle carrier proteins is that the fusion protein retains the ability to assemble into a nanoparticle and other beneficial properties that the carrier protein may have. In addition, the fused proteins or peptides need to be present on the outer surface of the fusion protein. Since there are usually more than one conserved peptide antigens from any given pathogens or disease conditions, there is a strong incentive to simultaneously fuse more than one peptide antigens to a carrier protein at different sites with all fused peptide antigens exposed on the surface to broaden the immune response and increase the vaccine efficacy, or increase detection sensitivity in the case of diagnostic tests. In addition, the fusion protein formed needs to be soluble and be sufficiently stable to withstand the purification process and storage as the final products. The fusion protein is also preferably thermostable which can be used to make vaccines that are stable at room or higher temperatures. Further, the fusion protein is preferably produced in the bacterial expression which is highly efficient and of low cost.

Thus, there are great needs for new and improved protein carrier systems that can achieve these advantageous attributes to produce more effective vaccine and diagnostic products. No one has previously focused on generation of fusion proteins with Dps, nor has anyone created a Dps fusion protein with two proteins or peptides fused simultaneously to different sites of Dps.

SUMMARY OF THE INVENTION

Therefore, the present invention provides a Dps fusion protein comprising at least one protein or peptide fused to Dps, wherein the Dps fusion protein is capable of self-assembly into nanoparticles and the protein or peptide is presented on the outer surface of the Dps fusion protein.

The present invention further provides a Dps fusion protein comprising two proteins or peptides fused separately and simultaneously to the N-terminus and C-terminus of Dps, wherein the Dps fusion protein is capable of self-assembly into nanoparticles and the two proteins or peptides are presented on the outer surface of the Dps fusion protein.

The present invention further provides Dps fusion proteins which are thermostable.

One embodiment of the present invention provides a Dps fusion protein comprising a viral fusion peptide, and the Dps fusion protein is soluble despite the poor solubility of the viral fusion peptide.

Another embodiment of the present invention provides a Dps fusion protein comprising a trimer-forming protein or peptide.

Another embodiment of the present invention provides a Dps fusion protein comprising two proteins or peptides derived from a group of proteins or peptides comprising M2e and HA2 of influenza virus, L2 protein of papilomavirus, gp41 of HIV, and WT1 protein of cancers.

Another embodiment of the present invention provides a Dps fusion protein comprising M2e and fusion peptide of influenza virus.

Another embodiment of the present invention provides a Dps fusion protein which is covalently conjugated with the alpha Gal epitope or its analog.

The present invention further provides a Dps fusion protein comprising a protein or peptide containing amino acids suitable for conjugation with carbohydrates, wherein the Dps fusion protein is conjugated with an oligosaccharide or polysaccharide derived from a bacterium, a fungus, a parasite, or a cancer as a glycoconjugate vaccine or diagnostic agent.

The present invention further provides a method of eliciting immune responses comprising administering to a human or animal an effective amount of the Dps fusion protein formulated in a pharmaceutically acceptable vehicle, carrier, excipient, adjuvant, or controlled release formulation.

The present invention further provides an immunogenic composition comprising a plurality of Dps fusion proteins, which optionally comprise the Dps derived from different bacteria or archaea.

The present invention and its various embodiments provide great advantages for development of new and improved vaccines, diagnostic tests, and other biomedical products. The fusion of two or more proteins or peptides with Dps at separate sites is extremely useful to broaden and increase immune responses and consequently the effectiveness of vaccines. It also makes Dps fusion proteins a highly effective diagnostic agent for use in diagnostic tests for diagnosis of infectious or non-infectious diseases. Furthermore, Dps fusion proteins are uniquely thermostable, being capable of withstanding treatment at a high temperature. The thermostability is a highly preferred feature for production and use of vaccines and other products as it allows the vaccine products to be stored and shipped at room or higher temperatures, thus facilitating the vaccine distribution and use worldwide, especially in emergency situations. The present invention also provides a new approach for development of glycoconjugate vaccines by using Dps fusion proteins that facilitate conjugation with carbohydrates.

The present invention is extremely useful for development of vaccines that are based on highly conserved peptide antigens to provide broad-spectrum or universal protection. A universal influenza vaccine comprising conserved peptide antigens such as fusion peptide and M2e fused with Dps is one such vaccine candidate which is urgently needed to provide an effective counter measure against potential future influenza pandemics as well as seasonal epidemics. Other examples of such vaccines that can benefit greatly from the present invention include those against HIV, HPV, TB, and cancers, all of which are of greatest public health concerns.

DETAILED DESCRIPTION OF THE INVENTION

Definition

Figure 1:
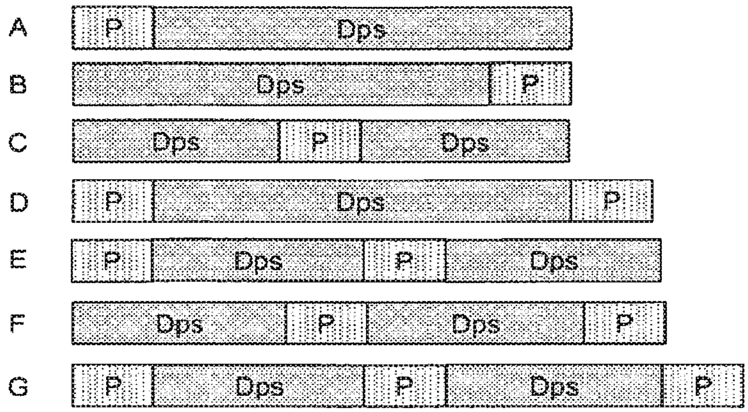
FIG. 1 shows examples of Dps fusion proteins. P, peptide. A, one protein or peptide fused at N-terminus of Dps; B, one protein or peptide fused at C-terminus of Dps; C, one protein or peptide fused at an internal site of Dps; D, two proteins or peptides fused at both N- and C-termini of Dps; E, two proteins or peptides fused at N-terminus and an internal site of Dps; F, two proteins or peptides fused at C-terminus and an internal site of Dps; G, Three proteins or peptides fused at N-terminus, C-terminus and an internal site of Dps, respectively. The protein or peptides may be same or different when more than one proteins or peptides are fused with Dps.

The words "antigen" and "immunogen" are used interchangeably herein and designates a molecule or substance that can induce specific immune responses.

The word "antigenicity" used herein refers to the ability to react with specific antibodies. The word "immunogenicity" used herein refers to the ability to induce specific immune responses.

The term "immune response" refers to antibody-mediated or cell-mediated immune responses or both.

The word "vaccine" refers to an antigen composition for therapeutic treatment of or active or passive prophylactic immunization against an infectious or non-infectious disease.

The word "protein" used herein refers to a chain of >100 amino acid residues linked together by peptide bond. The "peptide" refers to a chain of ≤100 amino acid residues linked together by peptide bond. The amino acid sequence in a protein or peptide is shown in the standard format, i.e., from amino terminus (N-terminus) to carboxyl terminus (C-terminus).

The term "fusion protein" designates a protein or peptide linked together with another protein or peptide by peptide bond between their respective N- and C-terminal amino acid residues or verse visa, or by insertion of the first protein or peptide into the internal region of the second protein or peptide by two peptide bonds at the N- and C-termini of the inserted protein or peptide. A peptide bond is a covalent chemical bond formed between carboxyl group of one amino acid and the amine group of another amino acid. The "fusion protein" used herein is produced by expression of the fusion protein gene in an expression host, in which the coding sequence for the first protein or peptide is linked to the coding sequence of the second protein or peptide.

The term "fusion site" refers to the site or amino acid residue of a protein or peptide to which another protein or peptide is linked by a peptide bond.

The word "nanoparticle" refers a particle with a size under 100 nm.

The word "carbohydrate" is used interchangeably with "saccharide" and has an empirical formula of $C_m(H_2O)_n$. Carbohydrate can be a monosaccharide, disaccharide, trisaccharide, oligosaccharide or polysaccharide. Monosaccharides are also referred to as simple sugars.

The word "polysaccharide" referred to a chain of >10 simple sugar residues linked together by the glycosidic bond. The "oligosaccharide" refers to a chain of ≤10 simple sugar residues linked together by the glycosidic bond.

The term "recombinant DNA technique" refers to the techniques for manipulating and combining two or more DNA sequences together that include recombination, PCR (polymerase chain reaction), in vitro mutagenesis, and direct DNA synthesis. These techniques are described in numerous published books and manuals, including the "Current protocols in molecular biology" (Ausubel eds. 2008. John Wiley & Son).

The term "disease condition" refers to any abnormal change in an animal or human that may be caused by an infectious agent or other underlying mechanisms.

The term "infectious agent" and "pathogen" are used interchangeably and refer to an infectious agent as well as disease causing agents such as toxins of various origins.

The word "a" or "an" means "one or more".

The term "controlled release formulation" refers to the formulations that provide a sustained or controlled release of the active ingredient in the formulation.

The words "cancer" and "tumor" are herein used interchangeably.

DETAILED DESCRIPTION

There are many challenges to use nanoparticle proteins like Dps as a carrier protein for vaccines, diagnostics, and other biomedical applications. Fusion with a foreign protein or peptide may disrupt nanoparticle formation, thus eliminating the carrier effect as a nanoparticle. The fused protein or peptide antigen may not be presented on the surface of the nanoparticle or retain its antigenicity. Thus, the present invention showed that Dps retained the ability to form nanoparticle when one protein or peptide was fused to either N- or C-terminus of Dps. The present invention further showed that Dps also retained the ability to form nanoparticles when two proteins or peptides were fused separately and simultaneously to both N- and C-termini of Dps. It was further shown that the proteins or peptides fused individually at either N-terminus or C-terminus or simultaneously at both termini of Dps were presented on the outer surface of the nanoparticles and were antigenic. They were also immunogenic as demonstrated with a Dps fusion protein incorporating two peptide antigens from influenza virus. The formation of nanoparticles was demonstrated by chromatography as well as electron microscopy. The surface presentation and antigenicity were shown with known specific antibodies against the peptide antigens in both dotblot (non-denaturing) and immunoblot (denaturing). Fusion and surface presentation of one or more protein or peptide antigens with Dps have not been previously demonstrated.

Considering that any change in the amino acid sequence of a protein, including fusion of a foreign protein or peptide to its terminus, can potentially disrupt the protein structure, it is unusual with Dps that retaining the nanoparticle formation together with surface presentation of the fused foreign protein or peptide can occur with fusion at the N-terminus as well as the C-terminus. It is especially unusual that this can also occur when two different proteins or peptides were fused separately and simultaneously to both N- and C-termini of Dps. This clearly distinguishes the Dps from ferritin which only allow surface presentation of the protein or peptide fused to its N-terminus (U.S. Pat. No. 7,608,268). As described above, the positions of the very ends of N- and/or C-terminal sequences of Dps are not known and may well extend into the interior of the nanoparticle structure as observed with the C-terminus of SsDps (Gauss et al., Biochemistry, 45:10815-10827, 2006). Dps is a relatively small nanoparticle. Thus, although not wanting to be bound by theory, it may be due to the limited interior space that foreign proteins or peptides fused to Dps terminal sequences can not be accommodated into the interior of the nanoparticles and therefore are left on their surfaces, even though the very end of terminal sequences may originally be located in the interior.

Dps fusion proteins may be generated in many different ways, including those presented in FIG. 1 and SEQ ID No: 1-7. For fusion at terminal sequences, the proteins or peptides may be fused next to the first or last amino acid of N- or C-terminus, respectively, or alternatively used to replace a portion of or the entire free N- or C-terminal sequences. Proteins or peptides may also be inserted into an internal site of Dps in one or more of the three loop sequences or the four helixes. Two proteins or peptides may be fused to Dps simultaneously at both termini with each at one separate terminus or with one at one terminus and the other at an internal site. The positions of the two proteins or peptides may be exchanged. Furthermore, three proteins or peptides may be fused simultaneously to Dps with each at one separate site—N-terminus, C-terminus, and an internal site. At the fusion site, a spacer or linker sequence may be introduced between the protein or peptide and the Dps protein. For example, one or more glycine or proline amino acids that are known as the helix breaker may be used as such spacers to allow the protein or peptide to fold separately from the Dps part of the fusion protein.

As indicated above and described in the Examples, nanoparticle formation was demonstrated by electron microscopy and chromatography. It is understood that these methods can not determine the exact number of subunits in the nanoparticles. Although it is likely that Dps fusion proteins also consist of 12 subunits, it is possible that the number of subunits could be more or less than 12, and the size of the nanoparticles may vary as well, depending on the protein or peptide fused. Thus, the Dps fusion proteins having a number of subunits other than 12 are also within the scope of current invention.

Any proteins or peptides from viruses, bacteria, fungi, parasites, cancers, and other disease conditions may be used for fusion with Dps to produce vaccines or diagnostic agents. However, peptides or peptide antigens (≤100 aa) may be preferred as they are smaller and can be readily fused with Dps without the potential of interfering with the nanoparticle formation. The peptide antigens are also much better defined and usually represent key or conserved antibody or T cell epitopes of the protein antigens for induction of the protective immunity. Some examples of the peptide antigens have been described above.

Dps is exclusively from prokaryotes and is not found in animals or humans. Thus, it is advantageous over other carrier proteins such as ferritins and heat shock proteins that are also found in animals and humans and may have a possibility of causing unwanted autoimmunity when used in vaccines. A further distinct advantage with Dps fusion protein vaccines is that Dps is available from many different families of bacteria or archaea. The Dps of any given origin may have its own distinct and novel characteristics that may be better suited for a given fusion protein vaccine or diagnostic agent. For example, some Dps proteins such as Dps of *E. Coli* (EcDps) (Swiss-Prot Accession #P0ABT2) have a relatively long N-terminus, whereas others such as *Mycobacterium smegmatis* Dps (MsDps) (Swiss-Prot Accession #P0C558) have a relatively long C-terminus. Thus, for a given fusion protein, Dps from different sources may be evaluated to select the most suitable one based on structural, biochemical and immunological properties. Furthermore, compositions comprising two or more fusion proteins with Dps from different families of bacteria or archaea can be created for vaccines and other biomedical applications. Such compositions can make use of the optimal Dps fusion protein for a given protein or peptide and therefore maximize the effect of each protein or peptide. Such compositions can also help eliminating the interference that may occur when two antigens linked separately to the same carrier protein are used together.

Thus, Dps may come from bacteria commonly associated with humans and animals, such as members of *Escherichia, Lactobacillus*, and *Bacteroides*. Dps may also come from extremophilic or hyperthermophilic bacteria or archaea such as *Sulfolobus solfataricus* and *Deinococcus radiodurans*. Dps may also come from pathogenic bacteria. Examples of bacterial pathogens may include *Streptococcus pneumonia, Helicobacter pylori, Campylobacter jejuni* and *Salmonella typhi*. Dps itself from these bacteria may provide a protective effect against the disease caused by them. Thus, besides acting as a carrier, Dps may also provide a protection against the bacteria from which it is originated. Unlike other Dps, the Dps from *Helicobacter pylori* (HpDps), also known as HP-NAP, possesses immunostimulating effect (de Bernard and D'Elios, Toxicon. 56:1186-1192, 2010). Thus, fusion proteins made with HpDps may possess the adjuvant effect that enhances the immune responses against the fused protein or peptide antigens.

Fusion of two protein or peptide antigens separately at both N- and C-termini along with surface presentation of both antigens is particularly useful for enhancing and broadening immune responses. That is, two copies of the same antigen can be fused separately to both N- and C-termini to double the number of the protein or peptide presented and thereby enhance the immune response. On the other hand, two different antigens can be fused separately to both N- and C-termini to broaden the immune response, which is particularly useful for developing vaccines that are intended to provide broad-spectrum or universal protection. A vaccine containing two different protein or peptide antigens may be made with one Dps fusion protein in which the two proteins or peptides are fused simultaneously at the separate sites of Dps or with two Dps fusion proteins with each containing one protein or peptide fused with Dps at one or more sites. It is also understood that each peptide may be fused to Dps as a single copy or multiple copies in tandem.

The ability of Dps for simultaneous fusion and surface presentation of more than one protein or peptide antigens brings great advantages to vaccines that are based on the conserved peptide antigens, since there are often more than one such conserved antigens from a pathogen, a cancer or other disease conditions. Influenza viruses undergo constant antigenic changes that pose a great challenge to developing vaccines for controlling influenza epidemics and pandemics. A universal influenza vaccine is urgently needed that can be used to control seasonal epidemics as well as pandemics without annual change of the vaccine antigens. The M2e and fusion peptide (FP) of influenza virus are among the most highly conserved epitopes or peptide antigens and therefore very suitable for a universal influenza vaccine. Thus, both M2e and fusion peptide were uniquely fused separately to N- and C-termini of Dps (M2e-SsDps-FP and M2e-EcDps-FP) in Examples 2 and 3, and resulting fusion protein was immunogenic as shown with M2e-SsDps-FP in Example 12. M2e is the 24 aa ectodomain of the minor envelope protein M2, and fusion peptide consists of the first 14 aa of the HA2 part of the major envelope protein HA. In addition, other conserved peptides such as helixes A, B, C and D of HA2 may also be incorporated or added in the same manner as described in Example 4. No one has previously fused two separate conserved peptides of influenza viruses with Dps or other nanoparticle protein carriers with both peptides exposed on the surface.

Another vaccine candidate is a universal HPV vaccine based on two or more highly conserved HPV L2 protein peptides. Thus, two such peptides, L2 (aa12-36) and L2 (aa108-120) were fused to the N- and C-termini of Dps, respectively. The L2 (12-36) and L2 (108-120) peptides from HPV L2 protein constitute the critical cell-binding site and each also bears the neutralizing epitope (Karanam et al., 2009). By incorporating these two highly conserved peptides, protection against different oncogenic HPV types can be broadened. Alternative or additional conserved peptides from the L2 and other proteins may also be used. No one has previously fused two separate conserved peptides of HPV L2 protein with Dps or other nanoparticle protein carriers with the resulting fusion protein being soluble as well as thermostable.

Still, another Dps fusion protein vaccine candidate is a HIV vaccine comprising one or more conserved protein or peptide antigens fused with Dps, including those recognized by broadly neutralizing monoclonal antibodies. These conserved HIV protein or peptide antigens include the epitopes recognized by broadly neutralizing monoclonal antibodies including 2F5, 4E10. Z13e1, VRC01, and PG16 (Shi et al., J Biol Chem. 285:24290-24298, 2010; Burton and Weiss, Science, 329: 770-773, 2010). Many of them are found in different regions of gp41 (FP, HR1, HR2, and MPER), including the fusion peptide. They can be readily fused with Dps as described in FIG. 1 and Example 6 as a vaccine that may provide a broader protective effect.

Still, another vaccine candidate example is a vaccine comprising tumor-associated antigens for treatment and prevention of cancers. The tumor-associated antigens are often made of peptides, including those from the WT1 protein. Several peptides from WT1 have been found to be effective as an immunotherapeutic vaccine against cancers, including RMFPNAPYL and SLGEQQYSV (Oka et al., Curr. Opinion in Immunol. 20:211-220). They can be readily fused with Dps as the vaccine candidates. Since the T-cell immunity is crucial in eliminating cancers, Dps from *Helicobacter pylori* (HpDps) may be preferred as it is known to have an immunomodulating effect that shifts the immune response toward the Th1 or cell-mediated immune response. The same strategy may be used for a vaccine against *Mycobacterium tuberculosis* (TB) since TB is an intracellular pathogen. The antigens that can be used together with HpDps for this vaccine may include those immunodominant epitopes from ESAT-6, Ag85A, and other proteins of TB.

For proteins or peptides that naturally form a trimeric structure, the present invention also embodies formation of a trimeric structure by the proteins or peptides fused at the N- or C-terminus of Dps. For such applications, fusion to the C-terminus may be preferred as the C-termini from three subunits come close together at the C-terminal 3-fold interface. Examples of the trimer-forming proteins or peptides include HA2 of influenza virus and gp41 of HIV. It is understood that a trimer may be formed by just trimer-forming regions of such proteins or peptides such as the helix A of HA2 and HR1 of gp41. Linker sequences such as that from yeast leucine zipper GCN4 may be introduced to facilitate the trimer formation. In addition, the length of protein or peptide or the terminal sequences of Dps may be extended or shortened to facilitate the trimer formation. The trimer formation will allow presentation of not only the linear epitopes, but also the conformational epitopes found only in the trimeric structure. The trimer formation can be demonstrated through structural analysis by electron microscopy, crystallography, and/or using antibodies that recognize the specific conformational epitopes.

Viral fusion peptides are found in all enveloped viruses which rely on cell fusion to initiate infection. Such enveloped viruses include influenza virus, HIV, Dengue virus, respiratory syncytial virus, and West nile virus. It is well known that the viral fusion peptide on its own is insoluble and difficult to handle due to its hydrophobicity (Chun et al., Vaccine 26:6068-6076, 2008), and influenza HA2 protein with the fusion peptide at its N-terminus could not be expressed on its own as a recombinant protein (Swalley et al. Biochemistry 43:5902-5911, 2004). The present invention showed that soluble Dps fusion proteins with the viral fusion peptide could be generated, especially when the fusion peptide was fused to the C-terminus of the Dps as shown in Examples 2, 3 and 7. Since the fusion peptide is among the most conserved sequences in enveloped viruses, such Dps fusion proteins will be extremely useful as a vaccine antigen and also as a diagnostic reagent for detection of these pathogens by measuring specific antibodies in animals or humans against the fusion peptide.

Thermostability is a highly desirable feature for vaccine products as it can significantly reduce the logistic requirements for storage, distribution, and use of the vaccine. The Dps of hyperthermophilic bacteria or archaea, which grow optimally at temperatures well above 75° C., can withstand treatment at a high temperature as observed with the Dps of *Sulfolobus solfataricus* (SsDps) (Wiedenheft et al., Proc Natl Acad Sci USA 102:10551-10556, 2005). We have further shown that SsDps was stable or remained as soluble nanoparticles after being treated at a high temperature (≥60° C.) for 1 hr. However, fusion with proteins or peptides may well eliminate this ability to withstand the heat. Thus, the present invention showed that SsDps fusion proteins remained stable when treated under the same conditions, even with proteins or peptides fused at both termini of the Dps. The fusion proteins remained as nanoparticles and proteins or peptides fused with the Dps remained antigenic after the treatment. The present invention further showed that fusion proteins with Dps from *E. Coli* (EcDps) was also stable under such conditions. This is also highly unexpected as *E. Coli* is a mesophile—an organism or microorganism which grows best at moderate temperatures (25-40° C.). Dps fusion proteins, however, could not withstand a temperature as high as the native Dps when they were tested at different temperatures (60, 70, 80, or 90° C.), with the exception of M2e-SsDps-FP as shown in Examples 9 and 10. Even though, it is remarkable that a substantial degree of the original thermostability was actually retained by the fusion proteins, which make them far more stable than most other proteins. Retaining the thermostability however did not occur with all fusion proteins as the M2e-ΔN22EcDps, in which the first 22 amino acids of the free N-terminus of EcDps was deleted and replaced with M2e, was not thermostable, suggesting that thermostability is dependent on preservation of terminal sequences and/or the manner by which the protein or peptide is fused.

Besides vaccines, Dps fusion proteins may be used as a diagnostic agent for diagnosis of infectious and non-infectious diseases. For example, they may be used as an antigen in immunoassays such as ELISA (enzyme-linked immunosorbent assay) and immunoblot for detecting antibodies specific to the protein or peptide fused to Dps. In a microarray format, Dps fusion proteins with different proteins or peptides may be used together for detecting a range of specific antibodies. Peptide aptamers may also be fused with Dps for diagnosis. They are short variable peptide domains of 10-20 amino acids that bind to a specific target or receptor. Dps fusion proteins may be further conjugated with an enzyme or a fluorescent dye or loaded with irons or other metals as a measure of detection or a signal emitter. Furthermore, Dps fusion proteins can be used to generate specific polyclonal or monoclonal antibodies against protein or peptides fused with Dps, which in turn can be used as a diagnostic agent to detect the protein or peptide, or pathogens or cells associated with it. Dps from hyperthermophiles or other extremophiles, such as SsDps, is preferred for the diagnostic application as hyperthermophiles or other extremophiles seldom come into contact with animals or humans, and therefore has no or less chance of cross reactivity.

Dps or Dps fusion proteins may be modified by substitution, insertion, or deletion of one or more amino acids using the recombinant DNA techniques well known in the arts. One such modification is to modify terminal and internal sequences of Dps to optimize the particle formation and antigen presentation of the fusion proteins. For example, additional amino acid residues may be added to N- or C-terminus to extend the free terminal sequences to ensure the full surface exposure of the terminus and the proteins or peptides fused to them, and for the same purpose, amino acids may be deleted from the N- or C-terminus in some cases. An additional modification is to make the chimeric Dps proteins such as one having one or both terminal sequences from one Dps and the internal sequence from another Dps to ensure that both N- and C-termini are properly extended on the surface. Another modification is to eliminate the iron binding activity by changing the amino acids involved in the iron binding. However, this function may be left intact as preventing generation of free radicals through iron binding can be beneficial to the vaccine and other products.

Dps fusion proteins may be further modified by conjugation or covalent linking with a carbohydrate molecule. One such carbohydrate molecule is the alpha Gal epitope (Galα1-3Galβ1-4GlcNAc) or its analog. Humans and primates naturally have a very high titer of anti-alpha Gal antibodies. Thus, linking this alpha Gal epitope to the fusion protein allows formation of the antigen-antibody complexes, which in turn can facilitate the antigen presentation and enhance immune responses against the protein or peptide fused with Dps. Although human anti-alpha Gal antibodies react most avidly with the Galα1-3Galβ1-4GlcNAc structure, they also react strongly with melibiose (Galα1-6Glc). As a result, melibiose has been used as a ligand for affinity purification of these human antibodies (Galili et al. J. Exp. Med. 160: 1519-1531). In Example 11, melibiose was successfully linked with the dual-peptide Dps fusion protein M2e-SsDps-FP and SsDps by reductive amination. The reductive amination links carbohydrate molecules to the ε-amine group of lysine residues on the proteins and is one of the most widely used and the mildest carbohydrate conjugation method. Neither of M2e or FP contains any lysine residues, and their structures are thus not affected by conjugation with this method.

Figure 2:
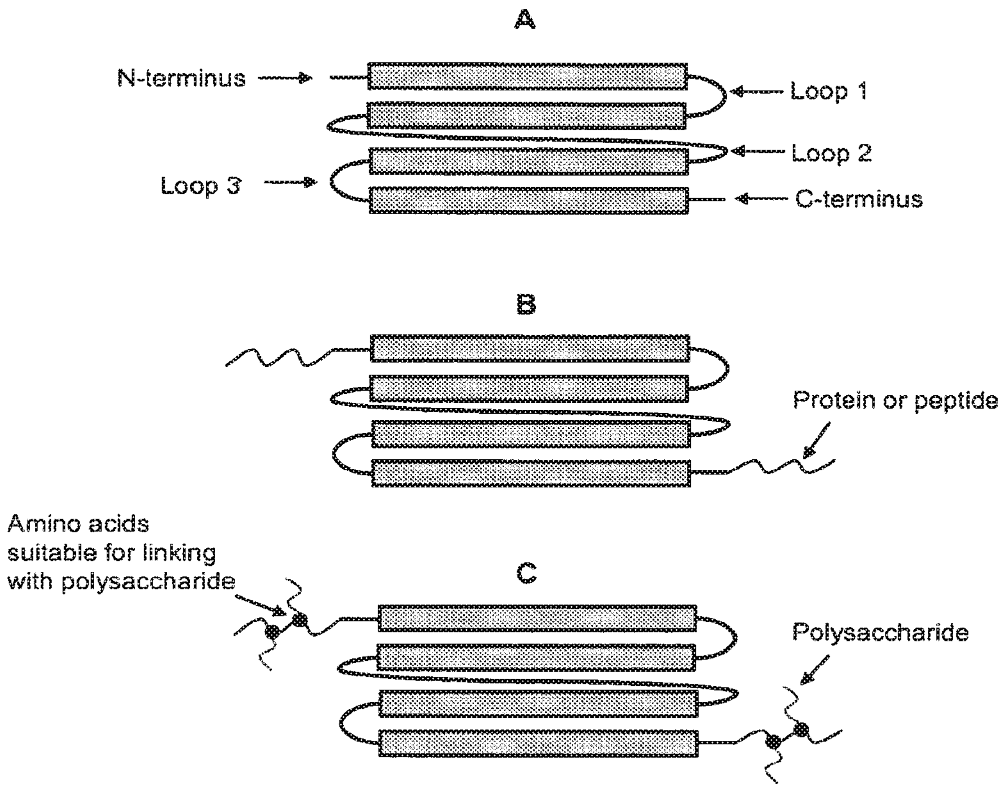
FIG. 2 shows schematic representation of a monomer from native Dps (A), Dps fusion protein with a protein or peptide fused at both N- and C-termini of Dps (B), and Dps fusion protein with a protein or peptide fused at both N- and C-termini of Dps, to which oligosaccharides or polysaccharides are linked through amino acids suitable for such linkage contained in the protein or peptide (C). Not shown in panel C, oligosaccharides or polysaccharides may also be linked to Dps at sites where suitable amino acids are present.

Furthermore, Dps fusion proteins may be used as a carrier protein for oligosaccharide or polysaccharide antigens to produce glycoconjugate vaccines, which consist of a carbohydrate antigen covalently linked to a protein carrier. Glycoconjugate vaccines are a major class of vaccines against bacterial infectious diseases and are being developed against other infectious and non-infectious diseases including fungi and cancers. By linking to a protein carrier, carbohydrate antigens become T cell-dependent, i.e., they exhibit the boosting effect upon repeated immunization or immune memory. Bacterial and fungal polysaccharide antigens may come from various bacterial and fungal pathogens, including *Streptococcus pneumonia. Neisseria meningitides, Campylobacter jejuni. Haemophilus influenzae*, group B *Streptococcus. Shigella flexneri. Bacillus anthracis. Pseudomonas aeruginosa. Salmonella typhi. Mycobacterium tuberculosis*, and *Candida albican*. The Example 11 demonstrated successful conjugation of a yeast mannan polysaccharide with Dps fusion protein M2e-SsDps-FP by reductive amination. A peptide rich in lysine or other suitable amino acids may be fused or inserted to either or both of N- and C-termini of Dps to further facilitate the conjugation as described in FIG. 2. Thus, besides existing conjugation sites within the Dps, a fixed number of additional conjugation sites are provided with the peptide fused to Dps. Examples of lysine-rich peptides can be readily found in viral and bacterial proteins, such as the first N-terminal 20 amino acids of the matrix protein of vesicular stomatitis virus (Swiss Prot accession #P03519). The peptide fused to Dps may contain other amino acids such as cysteine, aspartic acid, glutamic acid, and tyrosine that are suitable for conjugation with other methods (Pozsgay and Kubler-Kielb, In Carbohydrate-based vaccines, Rene Roy (ed.). pp 36-70. ACS, Washington D.C. 2008). It is preferred that the peptide contains at least two amino acids suitable for conjugation with carbohydrates. A distinctive advantage of using the Dps fusion protein as a carrier for bacterial glycoconjugate vaccines is that both Dps and polysaccharide antigen may come from the same bacterium. Fusion of a peptide containing suitable amino acids with Dps thus provides a consistent base number of suitable amino acid residues for linking carbohydrate antigens when Dps from different families of bacteria are used. This provides a significant advantage over using the native Dps as a carrier protein for glycoconjugate vaccines. Besides vaccines, Dps fusion protein glycoconjugates can also be used as diagnostic agents.

Dps fusion proteins are produced in the bacterial expression system at high yields, which is highly efficient and of low cost. They may be purified using standard purification techniques including precipitation, ion exchange, and size exclusion chromatography. Dps fusion proteins purified after expression in bacterial expression system may contain no or variable amount of irons. Thus, fusion proteins may be fully loaded with irons by mixing them with extraneous sources of irons such as $Fe(NH_4)_2(SO_4)$. Besides iron, they may also be loaded with other metal ions such as zinc, silver, nickel, copper, and cobalt. It is conceivable that the binding of iron or other metal ions may provide a stabilization effect to the fusion proteins. They may also serve as a signal emitter for the diagnostic test. Fusion proteins may also be treated with the agents commonly used to treat vaccine antigens such as formaldehyde, glutaraldehyde, ethylenimine, and β-propiolactone that may further stabilize the fusion proteins.

Vaccines with Dps fusion proteins can be prepared in saline, buffered saline, dry powder, controlled release formulation, or other pharmaceutically acceptable carriers or excipients for administration to humans or animals by intramuscular, intradermal, subcutaneous, transcutaneous, nasal, pulmonary, topical, or oral route. The vaccines may also be formulated with an adjuvant such as aluminum salts, calcium phosphate, oil-in-water emulsion, CpG, MPL (Monophosphoryl Lipid A), toll-like receptor ligands, cytokines, chemokines, and/or growth factors that are capable of increasing immune responses.

EXAMPLES

The followings are examples that serve to illustrate various embodiments, but not to limit, the scope of the present invention.

Example 1

Construction, Expression, Purification, and Characterization of Dps Fusion Proteins Proteins or peptides can be fused with Dps in different ways using standard recombinant DNA techniques (FIG. 1). A schematic view of Dps and Dps fusion protein is presented in FIG. 2. In this example, proteins or peptides were fused to either or both N- and C-termini of Dps. Examples of proteins or peptides fused with Dps and the resulting fusion proteins generated are listed in Tables 1 and 2. Two different Dps, EcDps of *E. Coli* (Genebank ID X69337.1; Swiss-Prot Accession #P0ABT2) and SsDps of *Sulfolbus solfataricus* (Genebank ID AE006642.1; Swiss-Prot ID P95855) were used in these examples.

1. Construction of Fusion Protein Genes

DNA sequences coding for proteins or peptides were fused to the DNA sequence coding for Dps to produce the fusion protein gene by PCR (polymerase chain reaction) amplification or DNA synthesis. The DNA sequences coding for the proteins or peptides were obtained by reverse translation or from the corresponding genes in the GenBank database. Thus, the DNA coding sequences for influenza M2e and fusion peptide may be obtained from published sequences of Genebank ID CY033623.1 and CY033622.1, respectively, and those for HPV L2 peptides may be obtained from Genebank ID AF536179.1.

TABLE 1

Proteins or peptides used for Dps fusion proteins

| Peptides | Amino acid sequence (No. amino acids) | Calculated Mw |
|---|---|---|
| Influenza M2e | MSLLTEVETPIRNEWGCRCNDSSD (24 aa) | 2.8 kDa |
| Influenza fusion peptide (FP) | GLFGAIAGFIEGGW (14 aa) | 1.4 kDa |
| HPV L2 (12-36) | RASATQLYKTCKQAGTCPPDIIPKV (25 aa) | 2.7 kDa |
| HPV L2 (17-36) | QLYKTCKQAGTCPPDIIPKV (19 aa) | 2.2 kDa |
| HPV L2 (108-120) | LVEETSFIDAGAP (13 aa) | 1.3 kDa |

TABLE 2

Examples of Dps fusion proteins

| Fusion proteins | Nanoparticle formation | Soluble protein | Thermo-stability |
|---|---|---|---|
| M2e - SsDps | Yes | Yes | Yes |
| SsDps - FP | Yes | Yes | Yes |
| FP-SsDps | Yes | Partial | Yes |
| M2e - SsDps - FP | Yes | Yes | Yes |
| M2e - EcDps | Yes | Yes | Yes |
| M2e - ΔN22EcDps | Yes | Yes | No |
| FP-EcDps | — | No | — |
| M2e - EcDps - FP | Yes | Yes | Yes |
| L2(12 - 36) - SsDps - L2(108 - 120) | Yes | Yes | Yes |
| L2(17 - 36) - SsDps - L2(108 - 120) | Yes | Yes | Yes |

Figure 3:
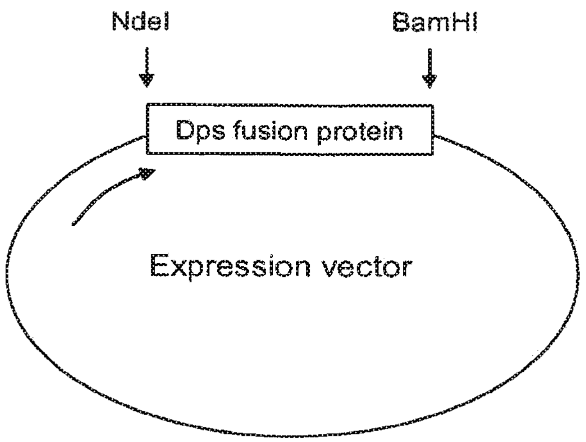
FIG. 3 shows a schematic representation of the Dps fusion protein gene in the expression vector plasmid for expression of the Dps fusion protein.

For Dps fusion protein genes, a NdeI site was introduced in-frame at the 5' end and a BamH1 site was placed at the 3' end for cloning into an expression vector (FIG. 3). The primers used for PCR incorporated the DNA sequence coding for the protein or peptide linked in-frame with that for the terminus of Dps (~15 nucleotides) at either 5' or 3' end. For longer peptides such as M2e, overlapping primers that overlaps by ~15 nucleotides were used to incorporate the entire coding sequence for the peptide. The DNA plasmids containing SsDps or EcDps gene that was either synthesized or cloned from bacterial DNA was used as the template in PCR. The fusion protein gene was amplified by PCR and cloned into TA clone vector (Invitrogen). After isolation of vector plasmids by mini-prep, the fusion protein gene was cloned into the expression vector such as pJexpress (DNA 2.0) and pET 11 or 25 (Novagen) using the NdeI and BamH1 sites for expression without any tag sequences. Alternatively, the entire fusion protein gene was synthesized using a DNA synthesis service provider such as DNA2.0 (CA). Prior to DNA synthesis, codons may be optimized for enhanced expression in *E. Coli.*

2. Expression and Purification of Dps Fusion Proteins

Expression was performed using standard recombinant protein expression protocols outlined by the expression vector and expression host cell providers. Expression vectors or plasmids were transformed into *E. coli* expression hosts (BL21). The bacteria were grown at 37° C. overnight in LB media, and transferred to fresh LB media at 1:3 ratio with a final OD 600 nm of 0.6-1.2. IPTG was added to 0.1-0.5 mM to induce the protein expression. After IPTG addition, bacteria were cultured at 37° C. for 4 hrs before harvesting for protein purification.

To purify fusion proteins, bacteria were pelleted by centrifugation at 3,000 g for 30 min and suspended in phosphate buffer saline (PBS; 20 mM phosphate, 150 mM NaCl, pH 7.4) or TN buffer (25 mM Tris, 150 mM NaCl, pH 8.0). Lysozyme was optionally added to 1 mg/ml followed by incubation at room temperature for 30 min. The suspensions were sonicated to lyse bacterial cells. The lysates were centrifuged at 15,000 g for 15 min. The supernatant was collected and filtered through a 0.2 μm filter. Dps fusion proteins in the supernatant were purified by gel filtration using the Bio-gel A1.5 m or Sepharose CL-6B column. Optionally, fusion proteins were first purified through DEAE-Sepharose CL-6B column before gel filtration. Fusion proteins were eluted from the DEAE-Sepharose column with a step NaCl gradient (0.2-0.5 M). Taking advantage of the thermostability of Dps fusion proteins (see Examples 9 and 10), the purification process was much simplified with a simple heat treatment step (60° C. for 10 minutes) that denatures most of the host proteins which were readily removed by centrifugation.

Purified fusion proteins were concentrated to ~10 mg/ml using a protein concentrator with 10 kDa cut-off. Protein concentrations were determined by bicinchoninic acid (BCA) assay.

3. Characterization of Fusion Proteins

SDS-PAGE (SDS-polyacrylamide gel electrophoresis) conducted under the denaturing conditions was used to examine the size or molecular weights of the monomers of Dps fusion proteins.

Gel filtration with Bio-Gel-A1.5 m column (1.8×85 cm) was used to examine the size or particle formation of Dps fusion proteins in relation to the native Dps. The peak of all fusion proteins examined was consistently eluted out earlier as compared to the native Dps by 1-5 fractions (2.5 ml each). These results showed that the Dps fusion proteins exhibited a size larger than the native Dps in correlation with addition of the peptides, and are therefore complexes or nanoparticles, like native Dps.

Transmission electron microscopy was performed to visualize the particle formation by negative staining. Proteins were stained with sodium phosphotungstate prior to examination.

Example 2

Generation of Dps Fusion Proteins with SsDps and Influenza Virus Peptides

Several Dps fusion proteins were generated with two highly conserved influenza virus peptides, M2e and fusion peptide (Tables 1 and 2). They include M2e-SsDps (SEQ ID No: 1) which had the M2e fused to the N-terminus of SsDps, SsDps-FP (SEQ ID No: 2) which had the fusion peptide fused to the C-terminus of SsDps, and dual peptide fusion protein M2e-SsDps-FP (SEQ ID No: 3) made by fusion of M2e and FP to N- and C-termini, respectively.

Figure 4:
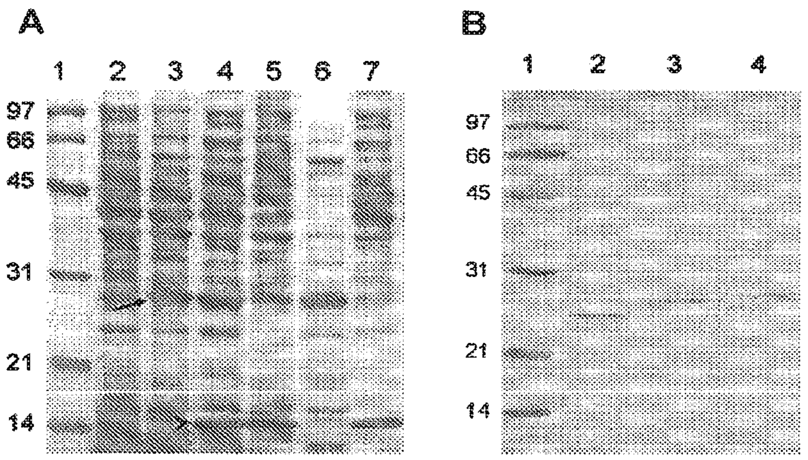
FIG. 4 shows expression and purification of Dps fusion proteins with influenza virus peptides. Panel A shows the expression of the dual-peptide fusion protein M2e-SsDps-FP. Lane 1, molecular weight marker; lanes 2 and 3, un-induced and induced *E. Coli*, respectively; lanes 4 & 5, supernatant and pellet of cell lysates from induced *E. Coli*, respectively; lanes 6 & 7, supernatant and pellet of the cell lysate supernatant (lane 4) treated at 65° C. for 10 min. Arrow indicates the fusion protein and arrow head indicates the lysozyme used for cell lysis. Panel B shows two purified SsDps fusion proteins in comparison with SsDps. Lane 1, molecular weight marker; lane 2, SsDps; lane 3, single-peptide fusion protein M2e-SsDps; lane 4, dual-peptide fusion protein M2e-SsDps-FP.

All these three fusion proteins were expressed at a high level, soluble, and readily purified. SDS-PAGE showed that the monomers of Dps fusion proteins exhibited a slightly increased molecular weight that was consistent with addition of peptide(s) as compared to the native Dps. The results with M2e-SsDps and M2e-SsDps-FP are shown in FIG. 4.

Figure 5:
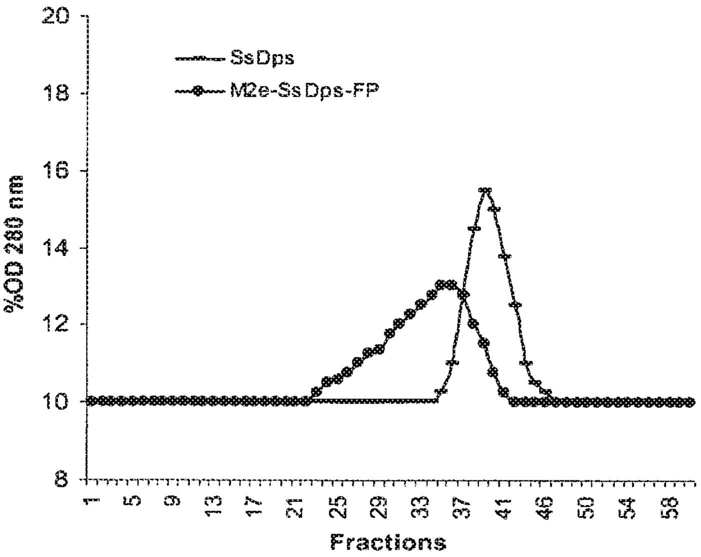
FIG. 5 shows chromatograms of SsDps and fusion protein M2e-SsDps-FP on Bio-gel A1.5 column.
Figure 6:
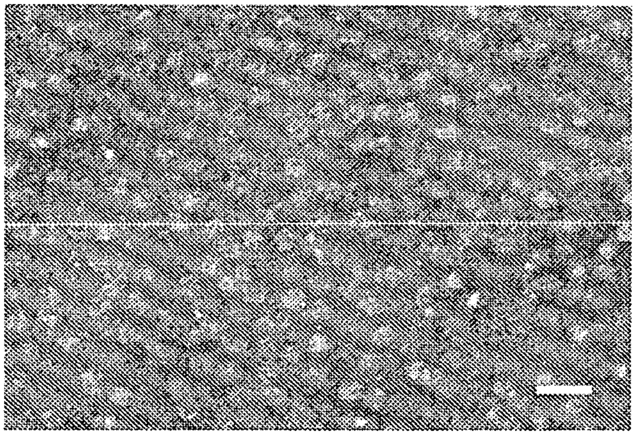
FIG. 6 shows an image of the dual-peptide Dps fusion protein M2e-SsDps-FP under electron microscope. Bar represents 20 nm.

On the Bio-gel A1.5 column, all fusion proteins were consistently eluted out at the same position or earlier by 1-5 fractions as compared to the native Dps (FIG. 5). These results showed that the Dps fusion proteins exhibited a size similar to or larger than the native Dps in correlation with addition of peptide antigens, and therefore are complexes or nanoparticles like native Dps. The particle formation was further confirmed by EM. The image of dual-peptide fusion protein M2e-SsDps-FP is shown in FIG. 6.

Example 3

Generation of Dps Fusion Proteins with EcDps and Influenza Virus Peptides

To demonstrate that fusion proteins can be generated with different Dps, three fusion proteins were generated with EcDps in the same manner, M2e-EcDps (SEQ ID No: 4), M2e-ΔN22EcDps (SEQ ID No: 5), and M2e-EcDps-FP (SEQ ID No: 6). They behaved similarly as the fusion proteins with SsDps described above based on SDS-PAGE and gel filtration with Bio-gel A1.5 column. All three of them were eluted out from the Bio-Gel A1.5 column at the same position or earlier by 1-5 fractions as compared to the native EcDps. In the M2e-ΔN22EcDps, the first 22 N-terminal amino acids of EcDps was deleted and replaced with the M2e.

Example 4

Generation of Dps Fusion Proteins with Additional Influenza Virus Peptides

Besides M2e and fusion peptide, other conserved proteins or peptides from influenza virus may also be fused with Dps as vaccine candidates or a part of vaccine candidates that provide universal or broad-spectrum protection. In addition, the same peptide may be fused to both N- and C-terminus such as M2e-SsDps-M2e. In this example, other peptides from HA2 of influenza virus are used, including helixes A, B, C, and D according to the nomenclature previously described (Bullough et al., Nature, 371:37-43, 1994) or any combination of them. The helix A is located next to the fusion peptide. Since these helixes are parts of HA2 trimer structure at neutral and/or acid pH, they may be adapted to form a trimer on the surface of Dps fusion protein, making use of the C-terminal 3 fold interface of Dps where the C-termini of three Dps subunits come close together. One example is SsDps-Helix A incorporating the helix A at the C-terminus of Dps. The fusion peptide may be added to produce fusion proteins SsDps-FP-Helix A or Helix A-SsDps-FP. The helixes B, C, and D may be fused with Dps in the same manner. The length of these HA2 helixes and adjacent sequence or the C-terminus of Dps may be extended or shortened to facilitate the trimer formation. The SsDps is used as an example for the fusion proteins described above and the Dps from other bacteria or archaea may also be used.

Example 5

Generation of Dps Fusion Proteins with Conserved Peptides from HPV L2 Protein

In this example, two highly conserved peptides from HPV L2 protein (aa17-36 and aa108-120) (Table 1) that constitute neutralizing epitopes and also HPV cell binding sites were fused with SsDps. A longer version of the first peptide, aa12-36, that constitutes the entire cell binding site at this region was also used. Thus, two dual peptide fusion proteins were generated with SsDps, L2(17-36)-SsDps-L2(108-120) and L2(12-36)-SsDps-L2(108-120) (SEQ ID No: 7).

Figure 7:
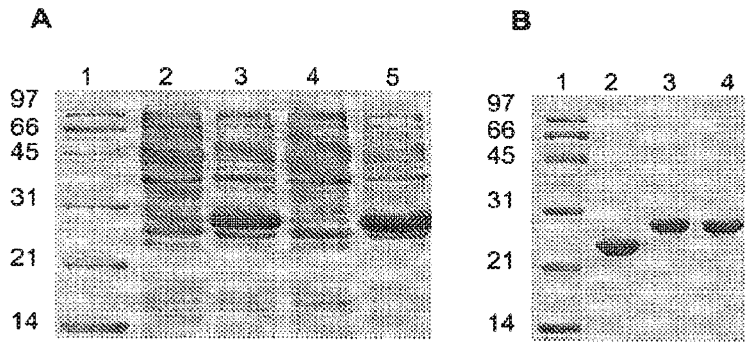
FIG. 7 shows expression and purification of Dps fusion proteins with HPV peptides. Panel A shows expression of two dual-peptide fusion proteins. Lane 1, molecular weight marker; lanes 2 and 3, un-induced and induced *E. Coli* with the fusion protein L2(12-36)-SsDps-L2(108-120); lanes 4 and 5: un-induced and induced *E. Coli* with the fusion protein L2 (17-36)-SsDps-L2 (108-120). Panel B shows purified fusion proteins, lane 1, molecular weight marker; lane 2, SsDps; lane 3, L2(12-36)-SsDps-L2(108-120), lane 4, L2(17-36)-SsDps-L2(108-120).

The expression and purification of these two fusion proteins are shown in FIG. 7. Like Dps fusion proteins with influenza virus peptides, these two HPV fusion proteins exhibited a increased molecular weight by SDS-PAGE, were eluted out earlier from the Bio-Gel A1.5 column than the native SsDps, and appeared as nanoparticles under EM.

Example 6

Generation of Dps Fusion Proteins with Other Proteins or Peptides

Besides the proteins or peptides described in the previous examples, many other proteins or peptides can be fused with Dps to produce vaccines, immunotherapeutics, as well as diagnostic agents. These include those from human immunodeficiency virus (HIV) and cancers.

HIV gp41 protein is more conserved than the gp120 and consists of distinct structural components—fusion peptide (~16 aa), fusion peptide proximal region (FPPR; ~13 aa), N-terminal heptad repeat (HR1; ~20 aa), the C-terminal heptad repeat (HR2; ~32 aa), and membrane proximal external region (MPER, ~20 aa). Conserved peptide sequences recognized by broadly neutralizing monoclonal antibodies 2F5 and 4E10 are located in MPER. MPER together with others such as fusion peptide can be fused with Dps as described in FIG. 1 to produce a vaccine that may provide a broad-spectrum protective effect. MPER may be fused to both termini of Dps (MPER-EcDps-MPER). In addition, fusion peptide, HR1 and/or HR2 may also be used either individually or in combination with MPER to yield fusion proteins such as MPER-EcDps-FP, EcDps-FP, and EcDps-HR2-MPER. As the HR1 and HR2 naturally form a trimer, they may be fused to Dps in a manner that facilitates trimer formation which may allow presentation of not only the linear peptide epitopes, but also the conformational epitopes found only in the trimeric structure. In light of the fact that HIV is highly variable, a vaccine may be made by combining two or more of these fusion proteins in order to include as many of these conserved peptides as possible, and consequently increase the efficacy of the vaccine.

Wilms tumor protein WT1 is found in various cancers and a major target for cancer immunotherapy. Several T-cell peptide epitopes have been identified in WT1 and shown to be effective as an immunotherapeutics in treatment of cancer patients, including RMFPNAPYL (RL9) and CMTWNQMNL (CL9). They can be fused either individually or together with Dps to yield fusion proteins such as RL9-EcDps-RL9, CL9-EcDps-CL9, and RL9-EcDps-CL9 to enhance their effect.

The EcDps is used as an example for the fusion proteins described above and the Dps from other bacteria or archaea may also be used. For applications in cancer immunotherapy where T-cell immunity is critical, the Dps from *Helicobacter*

*pylori* or HP-NAP may be preferred as it is known to have an immunomodulating effect that shifts the immune response toward the Th1 or cell-mediated immune response. Thus, fusion protein like RL9-HpDps-CL9 may be referred.

Example 7

Solubility of Dps Fusion Proteins

Proteins expressed in the bacterial system may be soluble by being present in the supernatant or insoluble by being present in the pellet or inclusion bodies, after high-speed centrifugation of lysed cells. It is preferred that Dps fusion proteins are fully soluble or at least partially soluble so that they can be readily purified. Insoluble fusion proteins can still be useful if they can be re-natured as nanoparticles after being solubilized under denaturing conditions. Dps fusion proteins described in the examples above are all fully soluble and readily purified by chromatography, 0.2 μm filtered, and concentrated. However, not all Dps fusions generated were fully soluble. Thus, FP-EcDps was insoluble, whereas the FP-SsDps was partially soluble. The solubility of the Dps fusion proteins is thus dependent on proteins or peptides, Dps, and the manner by which they are fused together. The fusion peptide is highly hydrophobic and insoluble on its own, a common feature for fusion peptides from all enveloped viruses. Thus, it is remarkable that fully and partially soluble Dps fusion proteins with the fusion peptide could actually be generated as shown with SsDps-FP, FP-SsDps, M2e-SsDps-FP, and M2e-EcDps-FP (Table 2).

Example 8

Antigenicity and Surface Exposure of Peptide Antigens Fused with Dps

The antigenicity of Dps fusion proteins with M2e and/or fusion peptide of influenza virus was evaluated in immunoblot and dotblot tests using an anti-M2e monoclonal antibody (16C2, Abcam) or a sheep anti-HA serum. The 16C2 antibody has been widely used to evaluate the M2e domain. The sheep anti-HA serum is the potency reagent for H1N1 (A/New Caledonia/20/99 (H1N1) that was raised against the purified HA protein.

For immunoblot, proteins were separated by SDS-PAGE under denaturing conditions before blotting onto a nylon membrane. The 16C2 antibody reacted with fusion proteins bearing M2e (M2e-SsDps and M2e-SsDps-FP), but not the native SsDps protein (FIG. 8A), and similarly, the anti-HA serum reacted only with the M2e-SsDps-FP, but not with M2e-SsDps or SsDps (FIG. 8A), indicating both M2e and fusion peptide were properly fused with Dps and antigenic.

Figure 8:
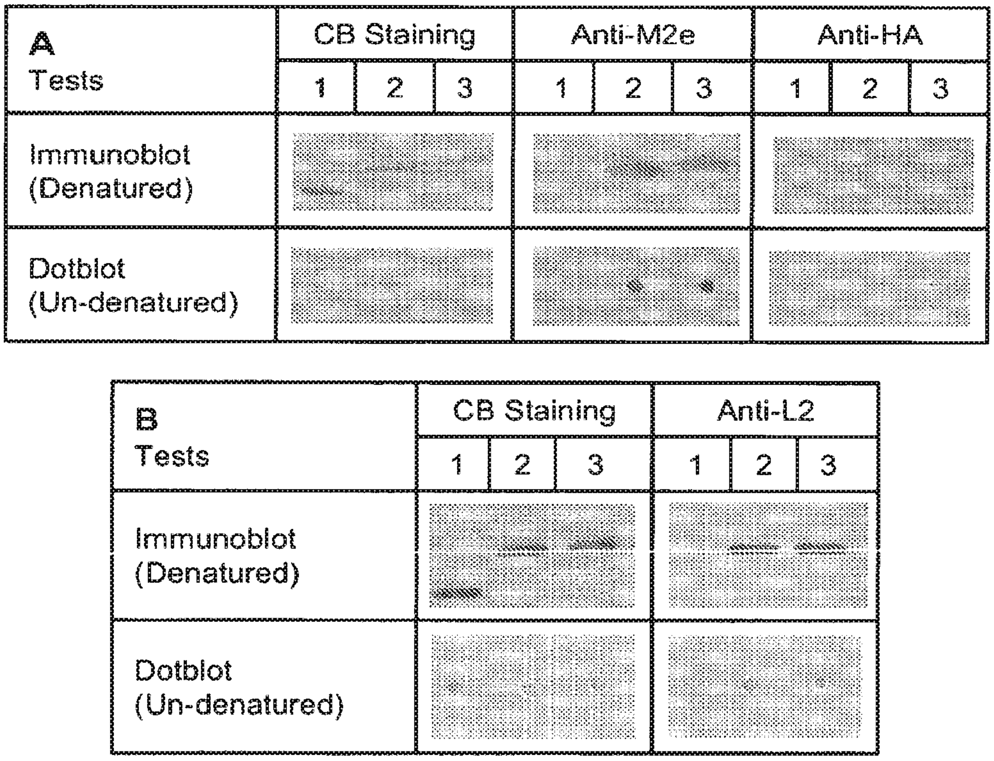
FIG. 8 shows the antigenicity of Dps fusion proteins. Panel A shows reaction of Dps fusion proteins with influenza virus peptides with specific antibodies by immunoblot and dotblot. Lane 1, SsDps; lane 2, M2e-SsDps; lane 3, M2e-Dps-FP. Dps fusion proteins were probed with an anti-M2e monoclonal antibody (16C2) or a sheep anti-H1N1 HA serum. Panel B shows the reaction of Dps fusion proteins with HPV L2 peptides with rabbit anti HPV L2 protein antibodies. Lane 1, SsDps; lane 2, L2 (12-36)-SsDps-L2 (108-120); lane 3, L2(17-36)-SsDps-L2(108-120). A piece of SDS-PAGE gel or dotblot membrane was stained with Coomassie blue (CB) to confirm the presence of the proteins.

In the dotblot, Dps fusion proteins were directly spotted onto cellulose membrane under non-denaturing conditions, i.e., the intact Dps fusion protein nanoparticles were tested. Similar results were obtained, i.e., specific antibodies reacted only with fusion proteins bearing the corresponding peptides (FIG. 8A). These results indicate that the peptides fused at both N- and C-termini were present on the surface of Dps fusion proteins and antigenic. As expected, the reaction with the anti-HA serum was weaker as it is raised against the whole HA molecule, not just the fusion peptide.

The Dps fusion protein with fusion peptide at C-terminus (SsDps-FP) was also tested. It only reacted with the anti-HA serum in both immunoblot and dotblot. In addition, Dps fusion proteins with EcDps (M2e-EcDps and M2e-EcDps-FP) behaved in the same way as those with SsDps in both immunoblot and dotblot, except that the reaction with the anti-HA serum appeared to be stronger for M2e-EcDps-FP.

These results together clearly indicated that M2e and fusion peptide fused to Dps at N- and/or C-termini are antigenic and present on the outer surface of fusion protein nanoparticles.

Similarly, the antigenicity of fusion proteins with HPV peptide antigens was evaluated in dotblot and immunoblot with a rabbit antiserum raised against the whole L2 protein. The results showed that the antibody reacted with both Dps fusion proteins (L2(12-36)-SsDps-L2(108-120) and L2(17-36)-SsDps-L2(108-120)) in both immunoblot and dot blot, but not SsDps (FIG. 8B). This indicates that the fused peptides are antigenic and displayed on the surface of Dps fusion protein nanoparticles.

Example 9

Thermostability of Dps Fusion Proteins with SsDps

To evaluate the thermostability of Dps fusion proteins, clarified cell lysates with the fusion proteins prepared in PBS were treated at 60° C. for various periods of times. Under stressed conditions such as heat and strong acid or base, proteins generally lose solubility and form precipitates. The results showed that SsDps and SsDps fusion proteins remained soluble or in the supernatant with no apparent degradation till the end of treatment (60 min), including the fusion proteins with two peptides fused separately at both ends. On the other hand, most of host cell proteins formed aggregates and precipitated after just 2 minutes when the protein solutions started to turn cloudy. The precipitates were removed by centrifugation at 12,000 g for 10 min.

Figure 9:
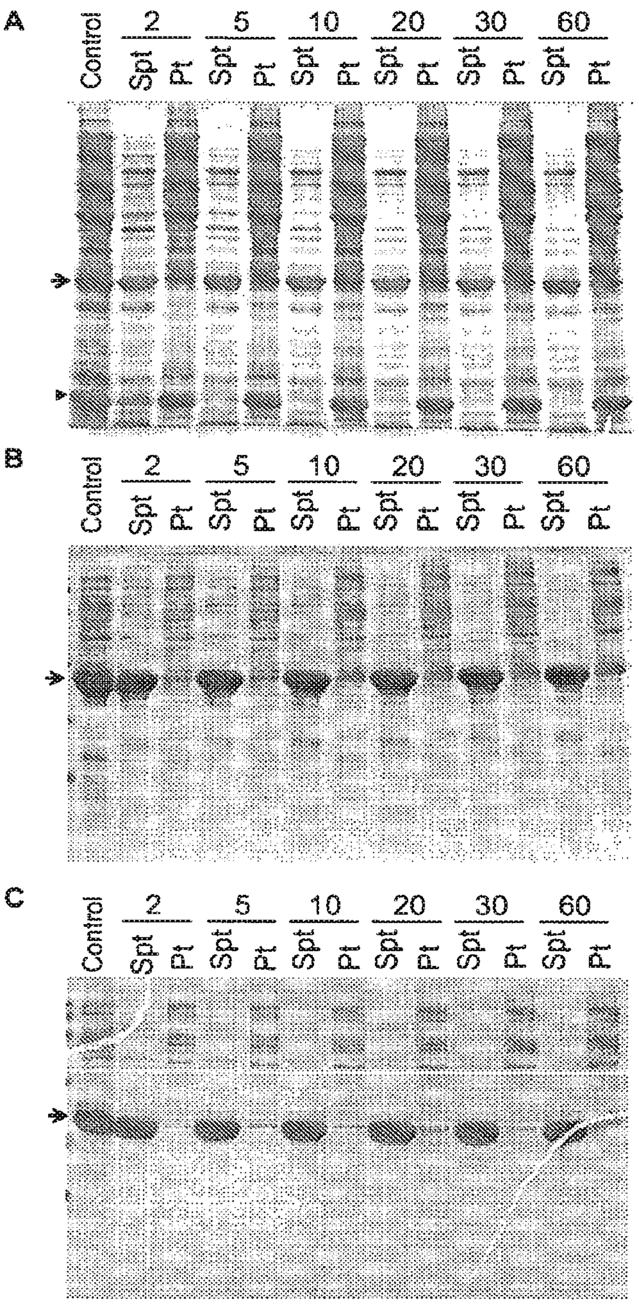
FIG. 9 shows the thermostability of Dps fusion proteins M2e-SsDps-FP (A), L2(12-36)-SsDps-L2(108-120)(B), and M2e-EcDps (C). Cell lysates with the fusion protein were treated at 60° C. for various times (minutes) and then centrifuged at 12,000 g for 10 min. The supernatant (Spt) and pellet (Pt) were separated by SDS-PAGE. Arrow indicates the Dps fusion protein and the arrow head indicates the lysozyme used for cell lysis.

The results with dual-peptide fusion proteins M2e-SsDps-FP and L2(12-36)-SsDps-L2(108-120) are shown in FIGS. 9A and 9B. It was evident that well over 50% of the fusion proteins clearly remained stable at the end of the heat treatment. This was confirmed by the densitometry measurement. The amount of loss at the end of or any time points during the treatment was actually none or minimal.

Importantly, the SsDps fusion proteins purified after treatment at 60° C. for 1 hr, including both M2e-SsDps-FP and L2(12-36)-SsDps-L2(108-120), remained as nanoparticles as confirmed by chromatography and EM and reacted with specific antibodies in both dotblot and immunoblot tests. These results demonstrated that Dps fusion proteins with SsDps were thermostable under the conditions used.

The thermostability was also examined by treating fusion proteins for 10 min at different temperatures (60, 70, 80, or 90° C.). It was found that SsDps could withstand the treatment at 80° C. for 10 min with less than 50% loss. It was remarkable that the fusion protein M2e-SsDps-FP was found just as stable as the SsDps, while others, including L2(12-36)-SsDps-L2(108-120), could still withstand the treatment at 70° C. for 10 min. These results therefore showed that SsDps fusion proteins retained at least a substantial degree of thermostability of the native SsDps. Considering that some of these fusion proteins have two peptides fused simultaneously at both termini, it is remarkable that such a high degree of heat resistance was actually retained, which make these fusion proteins far more stable than most other proteins.

Example 10

Thermostability of Dps Fusion Proteins with EcDps

*E. Coli* is a mesophile. The EcDps and EcDps fusion proteins are not expected to be thermostable. Thus, it was found that both native EcDps and two EcDps fusion proteins (M2e-Dps and M2e-EcDps-FP) were just as stable when treated at 60° C. for 1 hr. The result with M2e-EcDps is shown in FIG. 9C. The treatment at different temperatures described above was also performed. EcDps could withstand the treatment at 70° C. for 10 min with less than 50% loss. Both M2e-Dps and M2e-EcDps-FP fusion proteins were just slightly less stable than EcDps under the condition (70° C. for 10 min) by having just slightly more loss, which however was still well below 50%.

However, the M2e-ΔN22EcDps generated in Example 3 was not thermostable under the same condition used, i.e., more than 50% loss occurred after treatment at 60° C. for just 10 minutes, indicating that retaining the thermostability does not occur with all fusion proteins and is dependent on preservation of the terminal sequence of Dps.

Example 11

Conjugation of Dps Fusion Proteins with Carbohydrates

Lactose, melibiose, and yeast mannan were used as carbohydrate or saccharide examples for conjugation with Dps or Dps fusion proteins by reductive amination. Mannan was oxidized with 10 mM $NaIO_3$ in 10 mM sodium acetate (pH 6.0) at room temperature for 1 hr and then dialyzed against water after addition of glycerol (0.1%, v/v). Disaccharides melibiose and lactose were used without oxidization. For conjugation, saccharides were mixed with proteins in 200 mM NaCl and 50 mM phosphate (pH 8.0) followed optionally by addition of sodium cyanoborohydride (5 mg/ml). The mannan and proteins were used at 2-5 mg/ml, and disaccharides were used at 30-150 mg/ml. The mixtures were kept at room or 37° C. for various times. The conjugates were analyzed by agarose gel. The conjugates with mannan were purified using Bio-gel A1.5 column and those with disaccharides were recovered by dialysis against PBS.

Conjugation of SsDps and SsDps fusion proteins were obtained with all saccharides tested. Agarose gel electrophoresis in 1% agarose and 10 mM Tris-boric-EDTA buffer (89 mM, pH 8.3; Sigma Chemical Co) was a very effective method to evaluate the conjugation process, in which conjugation was indicated by the altered migration pattern of conjugates as compared to the un-conjugated Dps or Dps fusion proteins. The migration of molecules in agarose gels is influenced by size as well as charge. Thus, the protein may move faster or slower depending on the saccharide used, and this change in migration becomes greater as more saccharide molecules are linked.

Figure 10:
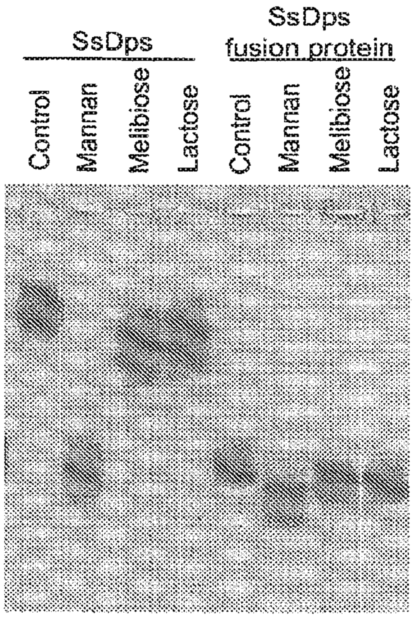
FIG. 10 shows conjugation of SsDps and fusion protein M2e-SsDps-FP with mannan, melibiose, and lactose. The reactions were conducted at 37° C. for 3 days. The reaction mixtures were separated by electrophoresis in 1% agarose gel.

The FIG. 10 shows that conjugation of SsDps and M2e-SsDps-FP with mannan, melibiose and lactose. The fusion protein was clearly conjugated with mannan, melibiose or lactose, like the SsDps, as shown by faster migration of the conjugates as compared to the un-conjugated controls. By SDS-PAGE, the SsDps and fusion protein conjugates with mannan were mostly trapped by the stacking gel due to their large sizes.

Figure 11:
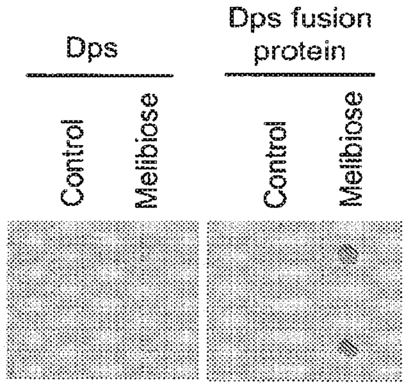
FIG. 11 shows reaction of SsDps and fusion protein M2e-SsDps-FP conjugated with melibiose with natural chicken anti-alpha Gal antibodies in dotblot. SsDps and fusion protein M2e-SsDps-FP with or without conjugation with melibiose were used.

The conjugates with melibiose reacted in dotblot with natural chicken anti-alpha Gal antibodies (FIG. 11). The anti-alpha Gal antibodies were isolated from normal chicken serum using melibiose-agarose column. Chickens, like humans, are also known to possess natural anti-alpha Gal antibodies. No reaction was observed with the un-conjugated Dps or Dps fusion protein controls. The fusion protein conjugate reacted more strongly than the Dps conjugate (FIG. 11). The reaction was drastically reduced or blocked if melibiose was added to the antibody solution. These results therefore further confirmed the conjugation of saccharides with Dps fusion protein and showed that the conjugated saccharides are reactive with specific antibodies.

Example 12

Immunogenicity of Dps Fusion Proteins

A group of Balb/c mice (n=5) were inoculated three times (days 0, 14, and 28) by intramuscular injection of the M2e-SsDps-FP fusion protein at 50 μg/mouse in combination with incomplete Freund adjuvant. Serum samples were collected one week before immunization and two or three weeks after the second or the third immunization. A pooled serum sample for each time point was generated with an equal part from each mouse and used in immunoblot and ELISA to detect specific antibodies. Immunoblot was conducted with inactivated H1N1 whole virion (A/New Caledonia/20/99) purified from infected MDCK cells as well as the HA protein of the same strain which was purified using lectin (RCA 120) affinity chromatography from infected MDCK cells following Triton X-100 treatment.

Figure 12:
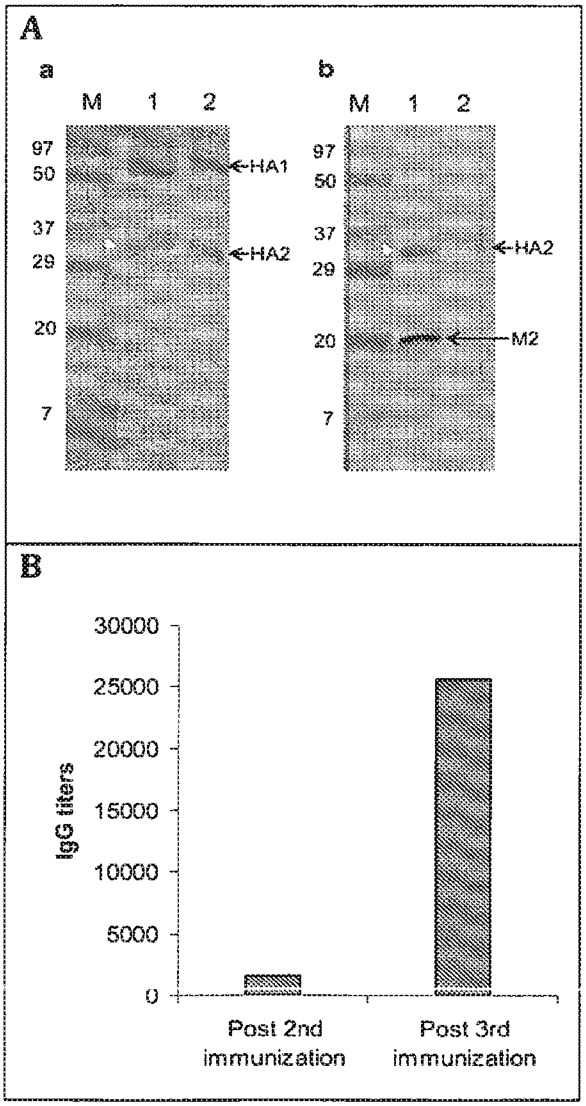
FIG. 12 shows reaction of specific serum generated against fusion protein M2e-SsDps-FP in mice with M2 and HA2 proteins of influenza virus by immunoblot (A) and with M2e peptide by ELISA (B). In panel A, a) Coomassie blue-stained gel; b) immunoblot; M, pre-stained molecular weight marker, lane 1, inactivated influenza whole virion (A/New Caledonia/20/99, H1N1); lane 2, HA protein of A/New Caledonia/20/99 (H1N1) strain. White arrow head indicates M1/HA2 in the inactivated whole virions.

The whole virion antigen contains all viral proteins, including the M2 and HA2. The results showed that the immune serum reacted with both M1/HA2 and M2 proteins (FIG. 12A), indicating that the fusion protein M2e-SsDps-FP induced specific antibodies against M2e and fusion peptide which are associated with M2 and HA2 proteins, respectively. In the H1N1 virus, HA2 protein co-migrates with M1 protein (FIG. 12A). The anti-M2e antibodies likely also reacted with M1 to some extent as the first nine N-terminal amino acids are identical between M1 and M2. Thus, the reaction of the induced anti-fusion peptide antibodies with HA2 was demonstrated by using the purified HA protein (FIG. 12 A).

The ELISA procedure for measuring anti-M2e antibodies has been well established. Thus, the anti-M2e antibodies raised by the fusion protein were also measured by ELISA. The 96-well plates (Nunc) were coated with synthetic M2e peptide (MSLLTEVETPIRNEWGCRCNDSSD) at 1 μg/ml with 100 μl per well in 10 mM carbonate buffer, pH9.6 at 4° C. overnight. Plates were washed with PBS-T (PBS+0.05% Tween 20) and blocked with 3% BSA in the PBS-T at 37° C. for 2 hrs. Serum samples were serially 2-fold diluted in PBS-T/1% BSA with a starting dilution of 1:400 and added to the plates in duplicate. After incubation at 37° C. for 1 hr, plates were washed and anti-mouse IgG alkaline phosphatase conjugate (Sigma Chemical Co) was added followed by incubation at 37° C. for 1 hr. Substrate pNPP (Pierce Chemical Co) was added and OD 410 nm was determined. The end point antibody titer was determined as the highest dilution that gave an OD value 2 times above the background of the blank wells. The results with pooled serum samples after the $2^{nd}$ and $3^{rd}$ immunization are presented in FIG. 12B. They showed that anti-M2e IgG antibodies were induced and much increased after the third immunization.

These results together showed that the Dps fusion protein is immunogenic and capable of inducing specific immune responses against proteins or peptides fused with Dps.

SEQUENCE LISTING

<160> NUMBER OF SEQ ID NOS: 15

<210> SEQ ID NO 1
<211> LENGTH: 211
<212> TYPE: PRT
<213> ORGANISM: Artificial Sequence
<220> FEATURE:
<223> OTHER INFORMATION: M2e peptide of influenza virus fused to
N-terminus of Dps protein of Sulfolobus solfataricus

<400> SEQUENCE: 1

Met Ser Leu Leu Thr Glu Val Glu Thr Pro Ile Arg Asn Glu Trp Gly
1 5 10 15

Cys Arg Cys Asn Asp Ser Ser Asp Gln Glu Lys Pro Gln Glu Pro Lys
20 25 30

Val Val Gly Val Glu Ile Leu Glu Lys Ser Gly Leu Asp Ile Lys Lys
35 40 45

Leu Val Asp Lys Leu Val Lys Ala Thr Ala Ala Glu Phe Thr Thr Tyr
50 55 60

Tyr Tyr Tyr Thr Ile Leu Arg Met His Leu Thr Gly Met Glu Gly Glu
65 70 75 80

Gly Leu Lys Glu Ile Ala Glu Asp Ala Arg Leu Glu Asp Arg Leu His
85 90 95

Phe Glu Leu Met Thr Gln Arg Ile Tyr Glu Leu Gly Gly Gly Leu Pro
100 105 110

Arg Asp Ile Arg Gln Leu Ala Asp Ile Ser Ala Cys Ser Asp Ala Tyr
115 120 125

Leu Pro Glu Asn Trp Lys Asp Pro Lys Glu Ile Leu Lys Val Leu Leu
130 135 140

Glu Ala Glu Gln Cys Ala Ile Arg Thr Trp Lys Glu Val Cys Asp Met
145 150 155 160

Thr Tyr Gly Lys Asp Pro Arg Thr Tyr Asp Leu Ala Gln Arg Ile Leu
165 170 175

Gln Glu Glu Ile Glu His Glu Ala Trp Phe Leu Glu Leu Leu Tyr Gly
180 185 190

Arg Pro Ser Gly His Phe Arg Arg Ser Ser Pro Gly Asn Ala Pro Tyr
195 200 205

Ser Lys Lys
210

<210> SEQ ID NO 2
<211> LENGTH: 202
<212> TYPE: PRT
<213> ORGANISM: Artificial Sequence
<220> FEATURE:
<223> OTHER INFORMATION: Fusion peptide of influenza virus fused to
C-terminus of Dps protein of Sulfolobus solfataricus

<400> SEQUENCE: 2

Met Gln Glu Lys Pro Gln Glu Pro Lys Val Val Gly Val Glu Ile Leu
1 5 10 15

Glu Lys Ser Gly Leu Asp Ile Lys Lys Leu Val Asp Lys Leu Val Lys
20 25 30

Ala Thr Ala Ala Glu Phe Thr Thr Tyr Tyr Tyr Tyr Thr Ile Leu Arg
35 40 45

Met His Leu Thr Gly Met Glu Gly Glu Gly Leu Lys Glu Ile Ala Glu
50 55 60

Asp Ala Arg Leu Glu Asp Arg Leu His Phe Glu Leu Met Thr Gln Arg

-continued

```
65                  70                  75                  80

Ile Tyr Glu Leu Gly Gly Gly Leu Pro Arg Asp Ile Arg Gln Leu Ala
                85                  90                  95

Asp Ile Ser Ala Cys Ser Asp Ala Tyr Leu Pro Glu Asn Trp Lys Asp
            100                 105                 110

Pro Lys Glu Ile Leu Lys Val Leu Leu Glu Ala Glu Gln Cys Ala Ile
        115                 120                 125

Arg Thr Trp Lys Glu Val Cys Asp Met Thr Tyr Gly Lys Asp Pro Arg
    130                 135                 140

Thr Tyr Asp Leu Ala Gln Arg Ile Leu Gln Glu Glu Ile Glu His Glu
145                 150                 155                 160

Ala Trp Phe Leu Glu Leu Leu Tyr Gly Arg Pro Ser Gly His Phe Arg
                165                 170                 175

Arg Ser Ser Pro Gly Asn Ala Pro Tyr Ser Lys Lys Gly Leu Phe Gly
            180                 185                 190

Ala Ile Ala Gly Phe Ile Glu Gly Gly Trp
        195                 200


<210> SEQ ID NO 3
<211> LENGTH: 224
<212> TYPE: PRT
<213> ORGANISM: Artificial Sequence
<220> FEATURE:
<223> OTHER INFORMATION: M2e peptide and fusion peptide of influenza
      virus fused respectively to N- and C-termini of Dps protein of
      Sulfolobus solfataricus

<400> SEQUENCE: 3

Met Ser Leu Leu Thr Glu Val Glu Thr Pro Ile Arg Asn Glu Trp Gly
1               5                   10                  15

Cys Arg Cys Asn Asp Ser Ser Asp Gln Glu Lys Pro Gln Glu Pro Lys
            20                  25                  30

Val Val Gly Val Glu Ile Leu Glu Lys Ser Gly Leu Asp Ile Lys Lys
        35                  40                  45

Leu Val Asp Lys Leu Val Lys Ala Thr Ala Ala Glu Phe Thr Thr Tyr
    50                  55                  60

Tyr Tyr Tyr Thr Ile Leu Arg Met His Leu Thr Gly Met Glu Gly Glu
65                  70                  75                  80

Gly Leu Lys Glu Ile Ala Glu Asp Ala Arg Leu Glu Asp Arg Leu His
                85                  90                  95

Phe Glu Leu Met Thr Gln Arg Ile Tyr Glu Leu Gly Gly Gly Leu Pro
            100                 105                 110

Arg Asp Ile Arg Gln Leu Ala Asp Ile Ser Ala Cys Ser Asp Ala Tyr
        115                 120                 125

Leu Pro Glu Asn Trp Lys Asp Pro Lys Glu Ile Leu Lys Val Leu Leu
    130                 135                 140

Glu Ala Glu Gln Cys Ala Ile Arg Thr Trp Lys Glu Val Cys Asp Met
145                 150                 155                 160

Thr Tyr Gly Lys Asp Pro Arg Thr Tyr Asp Leu Ala Gln Arg Ile Leu
                165                 170                 175

Gln Glu Glu Ile Glu His Glu Ala Trp Phe Leu Glu Leu Leu Tyr Gly
            180                 185                 190

Arg Pro Ser Gly His Phe Arg Arg Ser Ser Pro Gly Asn Ala Pro Tyr
        195                 200                 205

Ser Lys Lys Gly Leu Phe Gly Ala Ile Ala Gly Phe Ile Glu Gly Gly
    210                 215                 220
```

```
<210> SEQ ID NO 4
<211> LENGTH: 190
<212> TYPE: PRT
<213> ORGANISM: Artificial Sequence
<220> FEATURE:
<223> OTHER INFORMATION: M2e peptide of influenza virus fused to
      N-terminus of Dps protein of E. Coli

<400> SEQUENCE: 4

Met Ser Leu Leu Thr Glu Val Glu Thr Pro Ile Arg Asn Glu Trp Gly
1               5                   10                  15

Cys Arg Cys Asn Asp Ser Ser Asp Ser Thr Ala Lys Leu Val Lys Ser
            20                  25                  30

Lys Ala Thr Asn Leu Leu Tyr Thr Arg Asn Asp Val Ser Asp Ser Glu
        35                  40                  45

Lys Lys Ala Thr Val Glu Leu Leu Asn Arg Gln Val Ile Gln Phe Ile
    50                  55                  60

Asp Leu Ser Leu Ile Thr Lys Gln Ala His Trp Asn Met Arg Gly Ala
65                  70                  75                  80

Asn Phe Ile Ala Val His Glu Met Leu Asp Gly Phe Arg Thr Ala Leu
                85                  90                  95

Ile Asp His Leu Asp Thr Met Ala Glu Arg Ala Val Gln Leu Gly Gly
            100                 105                 110

Val Ala Leu Gly Thr Thr Gln Val Ile Asn Ser Lys Thr Pro Leu Lys
        115                 120                 125

Ser Tyr Pro Leu Asp Ile His Asn Val Gln Asp His Leu Lys Glu Leu
    130                 135                 140

Ala Asp Arg Tyr Ala Ile Val Ala Asn Asp Val Arg Lys Ala Ile Gly
145                 150                 155                 160

Glu Ala Lys Asp Asp Asp Thr Ala Asp Ile Leu Thr Ala Ala Ser Arg
                165                 170                 175

Asp Leu Asp Lys Phe Leu Trp Phe Ile Glu Ser Asn Ile Glu
            180                 185                 190


<210> SEQ ID NO 5
<211> LENGTH: 169
<212> TYPE: PRT
<213> ORGANISM: Artificial Sequence
<220> FEATURE:
<223> OTHER INFORMATION: M2e peptide of influenza virus fused to the
      N-terminus of Dps protein of E. Coli with deletion of the first 22
      amino acids at the N-terminus

<400> SEQUENCE: 5

Met Ser Leu Leu Thr Glu Val Glu Thr Pro Ile Arg Asn Glu Trp Gly
1               5                   10                  15

Cys Arg Cys Asn Asp Ser Ser Asp Asp Ser Glu Lys Lys Ala Thr Val
            20                  25                  30

Glu Leu Leu Asn Arg Gln Val Ile Gln Phe Ile Asp Leu Ser Leu Ile
        35                  40                  45

Thr Lys Gln Ala His Trp Asn Met Arg Gly Ala Asn Phe Ile Ala Val
    50                  55                  60

His Glu Met Leu Asp Gly Phe Arg Thr Ala Leu Ile Asp His Leu Asp
65                  70                  75                  80

Thr Met Ala Glu Arg Ala Val Gln Leu Gly Gly Val Ala Leu Gly Thr
                85                  90                  95

Thr Gln Val Ile Asn Ser Lys Thr Pro Leu Lys Ser Tyr Pro Leu Asp
```

```
            100                 105                 110

Ile His Asn Val Gln Asp His Leu Lys Glu Leu Ala Asp Arg Tyr Ala
        115                 120                 125

Ile Val Ala Asn Asp Val Arg Lys Ala Ile Gly Glu Ala Lys Asp Asp
    130                 135                 140

Asp Thr Ala Asp Ile Leu Thr Ala Ala Ser Arg Asp Leu Asp Lys Phe
145                 150                 155                 160

Leu Trp Phe Ile Glu Ser Asn Ile Glu
                165


<210> SEQ ID NO 6
<211> LENGTH: 276
<212> TYPE: PRT
<213> ORGANISM: Artificial Sequence
<220> FEATURE:
<223> OTHER INFORMATION: M2e peptide and fusion peptide of influenza
      virus fused respectively to N- and C-termini of Dps protein of
      E.Coli

<400> SEQUENCE: 6

Met Ser Leu Leu Thr Glu Val Glu Thr Pro Ile Arg Asn Glu Trp Gly
1               5                   10                  15

Cys Arg Cys Asn Asp Ser Ser Asp Asp Ser Glu Lys Lys Ala Thr Val
            20                  25                  30

Glu Leu Leu Asn Arg Gln Val Ile Gln Phe Ile Asp Leu Ser Leu Ile
        35                  40                  45

Thr Lys Gln Ala His Trp Asn Met Arg Gly Ala Asn Phe Ile Ala Val
    50                  55                  60

His Glu Met Leu Asp Gly Phe Arg Met Ser Leu Leu Thr Glu Val Glu
65                  70                  75                  80

Thr Pro Ile Arg Asn Glu Trp Gly Cys Arg Cys Asn Asp Ser Ser Asp
                85                  90                  95

Ser Thr Ala Lys Leu Val Lys Ser Lys Ala Thr Asn Leu Leu Tyr Thr
            100                 105                 110

Arg Asn Asp Val Ser Asp Ser Glu Lys Lys Ala Thr Val Glu Leu Leu
        115                 120                 125

Asn Arg Gln Val Ile Gln Phe Ile Asp Leu Ser Leu Ile Thr Lys Gln
    130                 135                 140

Ala His Trp Asn Met Arg Gly Ala Asn Phe Ile Ala Val His Glu Met
145                 150                 155                 160

Leu Asp Gly Phe Arg Thr Ala Leu Ile Asp His Leu Asp Thr Met Ala
                165                 170                 175

Glu Arg Ala Val Gln Leu Gly Gly Val Ala Leu Gly Thr Thr Gln Val
            180                 185                 190

Ile Asn Ser Lys Thr Pro Leu Lys Ser Tyr Pro Leu Asp Ile His Asn
        195                 200                 205

Val Gln Asp His Leu Lys Glu Leu Ala Asp Arg Tyr Ala Ile Val Ala
    210                 215                 220

Asn Asp Val Arg Lys Ala Ile Gly Glu Ala Lys Asp Asp Asp Thr Ala
225                 230                 235                 240

Asp Ile Leu Thr Ala Ala Ser Arg Asp Leu Asp Lys Phe Leu Trp Phe
                245                 250                 255

Ile Glu Ser Asn Ile Glu Gly Leu Phe Gly Ala Ile Ala Gly Phe Ile
            260                 265                 270

Glu Gly Gly Trp
        275
```

<210> SEQ ID NO 7
<211> LENGTH: 226
<212> TYPE: PRT
<213> ORGANISM: Artificial Sequence
<220> FEATURE:
<223> OTHER INFORMATION: Two peptides (amino acids 12-36 and 108-120) from L2 protein of human papillomavirus fused respectively to N- and C-termini of Dps protein of Sulfolobus solfataricus

<400> SEQUENCE: 7

```
Met Arg Ala Ser Ala Thr Gln Leu Tyr Lys Thr Cys Lys Gln Ala Gly
1               5                   10                  15

Thr Cys Pro Pro Asp Ile Ile Pro Lys Val Gln Glu Lys Pro Gln Glu
            20                  25                  30

Pro Lys Val Val Gly Val Glu Ile Leu Glu Lys Ser Gly Leu Asp Ile
        35                  40                  45

Lys Lys Leu Val Asp Lys Leu Val Lys Ala Thr Ala Ala Glu Phe Thr
    50                  55                  60

Thr Tyr Tyr Tyr Tyr Thr Ile Leu Arg Met His Leu Thr Gly Met Glu
65                  70                  75                  80

Gly Glu Gly Leu Lys Glu Ile Ala Glu Asp Ala Arg Leu Glu Asp Arg
                85                  90                  95

Leu His Phe Glu Leu Met Thr Gln Arg Ile Tyr Glu Leu Gly Gly Gly
            100                 105                 110

Leu Pro Arg Asp Ile Arg Gln Leu Ala Asp Ile Ser Ala Cys Ser Asp
        115                 120                 125

Ala Tyr Leu Pro Glu Asn Trp Lys Asp Pro Lys Glu Ile Leu Lys Val
    130                 135                 140

Leu Leu Glu Ala Glu Gln Cys Ala Ile Arg Thr Trp Lys Glu Val Cys
145                 150                 155                 160

Asp Met Thr Tyr Gly Lys Asp Pro Arg Thr Tyr Asp Leu Ala Gln Arg
                165                 170                 175

Ile Leu Gln Glu Glu Ile Glu His Glu Ala Trp Phe Leu Glu Leu Leu
            180                 185                 190

Tyr Gly Arg Pro Ser Gly His Phe Arg Arg Ser Ser Pro Gly Asn Ala
        195                 200                 205

Pro Tyr Ser Lys Lys Leu Val Glu Glu Thr Ser Phe Ile Asp Ala Gly
    210                 215                 220

Ala Pro
225
```

<210> SEQ ID NO 8
<211> LENGTH: 9
<212> TYPE: PRT
<213> ORGANISM: Artificial Sequence
<220> FEATURE:
<223> OTHER INFORMATION: Fusion Protein

<400> SEQUENCE: 8

```
Arg Met Phe Pro Asn Ala Pro Tyr Leu
1               5
```

<210> SEQ ID NO 9
<211> LENGTH: 9
<212> TYPE: PRT
<213> ORGANISM: Artificial Sequence
<220> FEATURE:
<223> OTHER INFORMATION: Fusion Protein

<400> SEQUENCE: 9

Ser Leu Gly Glu Gln Gln Tyr Ser Val
1 5

<210> SEQ ID NO 10
<211> LENGTH: 24
<212> TYPE: PRT
<213> ORGANISM: Artificial Sequence
<220> FEATURE:
<223> OTHER INFORMATION: Fusion Protein

<400> SEQUENCE: 10

Met Ser Leu Leu Thr Glu Val Glu Thr Pro Ile Arg Asn Glu Trp Gly
1 5 10 15

Cys Arg Cys Asn Asp Ser Ser Asp
20

<210> SEQ ID NO 11
<211> LENGTH: 14
<212> TYPE: PRT
<213> ORGANISM: Artificial Sequence
<220> FEATURE:
<223> OTHER INFORMATION: Fusion Protein

<400> SEQUENCE: 11

Gly Leu Phe Gly Ala Ile Ala Gly Phe Ile Glu Gly Gly Trp
1 5 10

<210> SEQ ID NO 12
<211> LENGTH: 25
<212> TYPE: PRT
<213> ORGANISM: Artificial Sequence
<220> FEATURE:
<223> OTHER INFORMATION: Fusion Protein

<400> SEQUENCE: 12

Arg Ala Ser Ala Thr Gln Leu Tyr Lys Thr Cys Lys Gln Ala Gly Thr
1 5 10 15

Cys Pro Pro Asp Ile Ile Pro Lys Val
20 25

<210> SEQ ID NO 13
<211> LENGTH: 20
<212> TYPE: PRT
<213> ORGANISM: Artificial Sequence
<220> FEATURE:
<223> OTHER INFORMATION: Fusion Protein

<400> SEQUENCE: 13

Gln Leu Tyr Lys Thr Cys Lys Gln Ala Gly Thr Cys Pro Pro Asp Ile
1 5 10 15

Ile Pro Lys Val
20

<210> SEQ ID NO 14
<211> LENGTH: 13
<212> TYPE: PRT
<213> ORGANISM: Artificial Sequence
<220> FEATURE:
<223> OTHER INFORMATION: Fusion Protein

<400> SEQUENCE: 14

Leu Val Glu Glu Thr Ser Phe Ile Asp Ala Gly Ala Pro
1 5 10

-continued

```
<210> SEQ ID NO 15
<211> LENGTH: 9
<212> TYPE: PRT
<213> ORGANISM: Artificial Sequence
<220> FEATURE:
<223> OTHER INFORMATION: Fusion Protein

<400> SEQUENCE: 15

Cys Met Thr Trp Asn Gln Met Asn Leu
1               5
```

What is claimed is:

1. A Dps fusion protein comprising at least one foreign peptide fused separately to Dps, wherein said Dps fusion protein is capable of self-assembly into nanoparticles, wherein said foreign peptide comprises at least two identical amino acids suitable for conjugation, wherein an isolated oligosaccharide or a polysaccharide is covalently linked to said suitable amino acids.

2. The Dps fusion protein of claim 1, wherein said Dps fusion protein is a vaccine.

3. The Dps fusion protein of claim 1, wherein said Dps fusion protein is a diagnostic agent.

4. The Dps fusion protein of claim 1, wherein said suitable amino acids are selected from a group comprising lysine, cysteine, tyrosine, aspartic acid, and glutamic acid.

5. The Dps fusion protein of claim 1, wherein said foreign peptide is fused to either or both of N-terminus and C-terminus of Dps and is presented on the outer surface of said Dps fusion protein.

6. The Dps fusion protein of claim 1, wherein said isolated oligosaccharide or polysaccharide is derived from a group comprising a bacterium, a virus, a fungus, a parasite, and a cancer.

7. The Dps fusion protein of claim 6 wherein said isolated oligosaccharide or polysaccharide and said Dps are derived from the same bacterium.

8. The Dps fusion protein of claim 1, wherein the Dps fusion protein comprises two peptides fused separately to Dps, each comprising at least two suitable amino acids for conjugation, wherein at least one of the peptides is a foreign peptide.

9. The Dps fusion protein of claim 8, wherein the two peptides are fused separately and simultaneously to N- and C-terminus of Dps.

* * * * *